(12) United States Patent
Wilhelm et al.

(10) Patent No.: US 9,526,441 B2
(45) Date of Patent: Dec. 27, 2016

(54) TARGETING LANDMARKS OF ORTHOPAEDIC DEVICES

(75) Inventors: Hoa La Wilhelm, Arlington, TN (US); James K. Rains, Cordova, TN (US); Daniel Hampton, Cordova, TN (US); Timothy J. Petteys, Bartlett, TN (US); Darin S. Gerlach, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 500 days.

(21) Appl. No.: 14/114,940

(22) PCT Filed: May 3, 2012

(86) PCT No.: PCT/US2012/036320
§ 371 (c)(1),
(2), (4) Date: Oct. 31, 2013

(87) PCT Pub. No.: WO2012/154496
PCT Pub. Date: Nov. 15, 2012

(65) Prior Publication Data
US 2014/0081121 A1    Mar. 20, 2014

Related U.S. Application Data

(60) Provisional application No. 61/483,228, filed on May 6, 2011.

(51) Int. Cl.
*A61B 5/04*    (2006.01)
*A61B 5/06*    (2006.01)
(Continued)

(52) U.S. Cl.
CPC ............... *A61B 5/062* (2013.01); *A61B 5/05* (2013.01); *A61B 5/4836* (2013.01);
(Continued)

(58) Field of Classification Search
CPC .. A61B 17/1707; A61B 17/1725; A61B 5/062
(Continued)

(56) References Cited

U.S. PATENT DOCUMENTS

| | | | |
|---|---|---|---|
| 3,219,969 | A | 11/1965 | Snavely |
| 4,353,110 | A | 10/1982 | Ellis |
| 4,532,599 | A | 7/1985 | Smith |
| 4,621,628 | A | 11/1986 | Brudermann |
| D297,047 | S | 8/1988 | Hon et al. |
| 4,794,930 | A | 1/1989 | Machida et al. |
| 4,803,976 | A | 2/1989 | Frigg et al. |

(Continued)

FOREIGN PATENT DOCUMENTS

| | | |
|---|---|---|
| CA | 2571508 | 1/2006 |
| CN | 2698283 Y | 5/2005 |

(Continued)

OTHER PUBLICATIONS

Notice of Reasons for Rejection for Japanese Application No. 2012-508518 mailed Dec. 10, 2013.

(Continued)

*Primary Examiner* — Ellen C Hammond
*Assistant Examiner* — Stuart S Bray
(74) *Attorney, Agent, or Firm* — Fish & Richardson P.C.

(57) ABSTRACT

A method for targeting a landmark of an orthopaedic implant comprises implanting the orthopaedic implant in a body. The orthopaedic implant having at least one landmark defining two or more locations for targeting and a first magnetic sensor located at a known distance from at least one of the two or more locations. The method includes comprises identifying one of the locations using a landmark identifier, the landmark identifier having at least one of a second magnetic sensor and a magnetic field generator, installing a transfixion element in the at least one landmark, and identifying a second location using the landmark identifier.

24 Claims, 6 Drawing Sheets

(51) Int. Cl.
  *A61B 17/80* (2006.01)
  *A61B 17/72* (2006.01)
  *A61B 5/05* (2006.01)
  *A61B 5/00* (2006.01)
  *A61B 17/86* (2006.01)
  *A61B 17/17* (2006.01)
  *A61B 17/00* (2006.01)

(52) U.S. Cl.
  CPC ...... *A61B 17/1707* (2013.01); *A61B 17/1725* (2013.01); *A61B 17/72* (2013.01); *A61B 17/7241* (2013.01); *A61B 17/80* (2013.01); *A61B 17/8057* (2013.01); *A61B 17/86* (2013.01); *A61B 34/20* (2016.02); *A61B 90/06* (2016.02); *A61B 90/39* (2016.02); *A61B 17/1703* (2013.01); *A61B 34/10* (2016.02); *A61B 2017/00199* (2013.01)

(58) Field of Classification Search
  USPC .................................. 606/97, 309; 600/424
  See application file for complete search history.

(56) References Cited

U.S. PATENT DOCUMENTS

| | | | |
|---|---|---|---|
| 5,049,151 A | 9/1991 | Durham et al. | |
| 5,127,913 A | 7/1992 | Thomas | |
| 5,217,009 A | 6/1993 | Kronberg | |
| 5,251,127 A | 10/1993 | Raab | |
| 5,281,224 A | 1/1994 | Faccioli et al. | |
| 5,361,766 A | 11/1994 | Nichols et al. | |
| 5,383,917 A | 1/1995 | Desai et al. | |
| 5,411,503 A * | 5/1995 | Hollstien ............ A61B 17/1707 606/80 | |
| 5,417,688 A | 5/1995 | Elstrom et al. | |
| 5,433,720 A * | 7/1995 | Faccioli ............ A61B 17/1707 606/87 | |
| 5,514,145 A | 5/1996 | Durham et al. | |
| 5,580,156 A | 12/1996 | Suzuki et al. | |
| 5,584,838 A | 12/1996 | Rona et al. | |
| 5,585,783 A | 12/1996 | Hall | |
| 5,957,836 A | 9/1999 | Johnson | |
| 5,957,934 A | 9/1999 | Rapoport | |
| 6,009,878 A | 1/2000 | Weijand et al. | |
| 6,036,696 A | 3/2000 | Lambrecht et al. | |
| 6,039,742 A | 3/2000 | Krettek et al. | |
| 6,074,394 A * | 6/2000 | Krause ............ A61B 17/1725 606/86 R | |
| 6,081,741 A | 6/2000 | Hollis | |
| 6,106,528 A * | 8/2000 | Durham ............ A61B 17/1707 606/62 | |
| 6,157,853 A | 12/2000 | Blume et al. | |
| 6,162,228 A | 12/2000 | Durham | |
| 6,168,595 B1 | 1/2001 | Durham et al. | |
| 6,174,335 B1 | 1/2001 | Varieur et al. | |
| 6,212,419 B1 | 4/2001 | Blume et al. | |
| 6,233,490 B1 | 5/2001 | Kasevich | |
| 6,266,551 B1 | 7/2001 | Osadchy et al. | |
| 6,267,770 B1 | 7/2001 | Truwit | |
| 6,304,091 B1 | 10/2001 | Shahoian et al. | |
| 6,311,082 B1 | 10/2001 | Creighton et al. | |
| 6,474,341 B1 | 11/2002 | Hunter et al. | |
| 6,503,249 B1 * | 1/2003 | Krause ............ A61B 17/1725 606/62 | |
| 6,575,973 B1 | 6/2003 | Shekalim | |
| 6,636,757 B1 | 10/2003 | Jascob et al. | |
| 6,675,491 B2 | 1/2004 | Sasaki et al. | |
| 6,694,168 B2 | 2/2004 | Traxel et al. | |
| 6,718,194 B2 | 4/2004 | Kienzle | |
| 6,747,253 B1 | 6/2004 | Firth et al. | |
| 6,807,446 B2 | 10/2004 | Fenn et al. | |
| 6,890,332 B2 | 5/2005 | Truckai et al. | |
| 6,991,655 B2 | 1/2006 | Iverson | |
| 7,001,346 B2 | 2/2006 | White | |
| 7,029,478 B2 | 4/2006 | Hollstien et al. | |
| 7,060,075 B2 | 6/2006 | Govari et al. | |
| D528,211 S | 9/2006 | Solar et al. | |
| 7,130,676 B2 | 10/2006 | Barrick | |
| 7,152,608 B2 | 12/2006 | Hunter et al. | |
| 7,217,276 B2 | 5/2007 | Henderson et al. | |
| 7,253,611 B2 | 8/2007 | Ma | |
| 7,294,133 B2 | 11/2007 | Zink et al. | |
| 7,295,184 B2 | 11/2007 | Suprun et al. | |
| 7,358,481 B2 | 4/2008 | Yeoh et al. | |
| 7,477,926 B2 | 1/2009 | McCombs | |
| 7,532,997 B2 | 5/2009 | Li et al. | |
| 7,542,791 B2 | 6/2009 | Mire et al. | |
| 7,549,960 B2 | 6/2009 | Govari | |
| 7,559,931 B2 | 7/2009 | Stone | |
| 7,575,550 B1 | 8/2009 | Govari | |
| 7,634,306 B2 | 12/2009 | Sarin et al. | |
| 7,686,818 B2 | 3/2010 | Simon et al. | |
| 7,702,379 B2 | 4/2010 | Avinash et al. | |
| 7,727,240 B1 | 6/2010 | Benton | |
| 7,729,742 B2 | 6/2010 | Govari | |
| 7,780,681 B2 | 8/2010 | Sarin et al. | |
| 7,785,330 B2 | 8/2010 | Sherman et al. | |
| 7,835,785 B2 | 11/2010 | Scully et al. | |
| 7,840,254 B2 | 11/2010 | Glossop | |
| 7,846,162 B2 | 12/2010 | Nelson et al. | |
| 7,918,853 B2 | 4/2011 | Watanabe | |
| 7,925,068 B2 | 4/2011 | Hoctor et al. | |
| 7,927,338 B2 | 4/2011 | Laffargue et al. | |
| 7,949,386 B2 | 5/2011 | Buly et al. | |
| 7,955,280 B2 | 6/2011 | Radinsky et al. | |
| 8,007,448 B2 | 8/2011 | Moctezuma de La Barrera | |
| 8,066,706 B2 | 11/2011 | Schlienger et al. | |
| 8,167,823 B2 | 5/2012 | Nycz et al. | |
| 8,176,922 B2 | 5/2012 | Sherman et al. | |
| 8,197,494 B2 | 6/2012 | Jaggi | |
| 8,211,108 B2 | 7/2012 | Matityahu | |
| 8,241,296 B2 | 8/2012 | Wasielewski | |
| 8,251,994 B2 | 8/2012 | McKenna et al. | |
| 8,301,262 B2 | 10/2012 | Mi et al. | |
| 8,337,426 B2 | 12/2012 | Nycz | |
| 8,623,023 B2 | 1/2014 | Ritchey | |
| 8,890,511 B2 | 11/2014 | Belew | |
| 8,997,362 B2 * | 4/2015 | Briggs ................ G01B 11/005 33/503 | |
| 2002/0052604 A1 | 5/2002 | Simon et al. | |
| 2002/0077540 A1 | 6/2002 | Kienzle | |
| 2002/0173792 A1 | 11/2002 | Severns et al. | |
| 2003/0105470 A1 | 6/2003 | White | |
| 2003/0120150 A1 | 6/2003 | Govari | |
| 2003/0135211 A1 | 7/2003 | Cho | |
| 2003/0153829 A1 | 8/2003 | Sarin et al. | |
| 2003/0164172 A1 | 9/2003 | Chumas et al. | |
| 2003/0208122 A1 | 11/2003 | Melkent et al. | |
| 2004/0011365 A1 * | 1/2004 | Govari ............ A61B 17/1707 128/899 | |
| 2004/0034355 A1 | 2/2004 | Govari et al. | |
| 2004/0097952 A1 | 5/2004 | Sarin et al. | |
| 2004/0147926 A1 | 7/2004 | Iversen | |
| 2004/0230199 A1 | 11/2004 | Jansen et al. | |
| 2004/0243148 A1 | 12/2004 | Wasielewski | |
| 2004/0254584 A1 | 12/2004 | Sarin et al. | |
| 2005/0027301 A1 | 2/2005 | Stihl | |
| 2005/0027304 A1 | 2/2005 | Leloup et al. | |
| 2005/0035115 A1 | 2/2005 | Anderson et al. | |
| 2005/0035116 A1 | 2/2005 | Brown et al. | |
| 2005/0043726 A1 | 2/2005 | McHale et al. | |
| 2005/0059885 A1 | 3/2005 | Melkent et al. | |
| 2005/0070916 A1 | 3/2005 | Hollstien et al. | |
| 2005/0075562 A1 | 4/2005 | Szakelyhidi et al. | |
| 2005/0075632 A1 | 4/2005 | Russell et al. | |
| 2005/0080335 A1 * | 4/2005 | Simon ................ A61B 17/1707 600/424 | |
| 2005/0080427 A1 | 4/2005 | Govari et al. | |
| 2005/0085714 A1 | 4/2005 | Foley et al. | |
| 2005/0085715 A1 | 4/2005 | Dukesherer et al. | |
| 2005/0099290 A1 | 5/2005 | Govari | |
| 2005/0124988 A1 | 6/2005 | Terrill et al. | |
| 2005/0143726 A1 | 6/2005 | Bortkiewicz | |

(56) References Cited

U.S. PATENT DOCUMENTS

| | | |
|---|---|---|
| 2005/0148855 A1 | 7/2005 | Kienzle |
| 2005/0149050 A1 | 7/2005 | Stifter et al. |
| 2005/0197569 A1 | 9/2005 | McCombs |
| 2005/0228270 A1 | 10/2005 | Lloyd et al. |
| 2005/0242087 A1 | 11/2005 | Anderson et al. |
| 2005/0245821 A1 | 11/2005 | Govari et al. |
| 2005/0261700 A1 | 11/2005 | Tuma et al. |
| 2006/0015031 A1 | 1/2006 | Kienzle |
| 2006/0052782 A1 | 3/2006 | Morgan et al. |
| 2006/0074405 A1 | 4/2006 | Malackowski et al. |
| 2006/0084867 A1 | 4/2006 | Tremblay |
| 2006/0095047 A1 | 5/2006 | de la Barrera |
| 2006/0106400 A1* | 5/2006 | Fernandez ......... A61B 17/1703 606/97 |
| 2006/0122541 A1 | 6/2006 | Tuma |
| 2006/0142656 A1 | 6/2006 | Malackowski et al. |
| 2006/0190011 A1 | 8/2006 | Ries |
| 2006/0264731 A1 | 11/2006 | Murphy |
| 2006/0282168 A1 | 12/2006 | Sherman |
| 2006/0287613 A1 | 12/2006 | Amiot et al. |
| 2006/0293593 A1 | 12/2006 | Govari et al. |
| 2006/0293614 A1 | 12/2006 | Radinsky et al. |
| 2007/0093709 A1 | 4/2007 | Abernathie |
| 2007/0129629 A1 | 6/2007 | Beauregard et al. |
| 2007/0162018 A1 | 7/2007 | Jensen et al. |
| 2007/0167744 A1 | 7/2007 | Beauregard et al. |
| 2007/0191827 A1 | 8/2007 | Lischinsky et al. |
| 2007/0208251 A1 | 9/2007 | Anderson et al. |
| 2007/0219409 A1 | 9/2007 | Shimizu et al. |
| 2007/0225595 A1 | 9/2007 | Malackowski et al. |
| 2007/0249967 A1 | 10/2007 | Buly et al. |
| 2007/0255132 A1 | 11/2007 | Shalgi et al. |
| 2007/0276370 A1 | 11/2007 | Altarac et al. |
| 2007/0282440 A1* | 12/2007 | Visentin ............. A61B 17/1707 623/16.11 |
| 2008/0021309 A1 | 1/2008 | Amiot et al. |
| 2008/0039857 A1 | 2/2008 | Giersch et al. |
| 2008/0051910 A1 | 2/2008 | Kammerzell et al. |
| 2008/0071142 A1 | 3/2008 | Gattani et al. |
| 2008/0086145 A1* | 4/2008 | Sherman ............ A61B 17/1707 606/97 |
| 2008/0146969 A1 | 6/2008 | Kurtz |
| 2008/0221628 A1 | 9/2008 | Milbocker et al. |
| 2008/0228195 A1 | 9/2008 | von Jacko et al. |
| 2008/0255560 A1 | 10/2008 | Myers et al. |
| 2008/0269596 A1 | 10/2008 | Revie et al. |
| 2008/0281326 A1 | 11/2008 | Watanabe et al. |
| 2008/0281334 A1 | 11/2008 | Zheng et al. |
| 2009/0024023 A1 | 1/2009 | Welches et al. |
| 2009/0054910 A1 | 2/2009 | Zheng et al. |
| 2009/0088756 A1 | 4/2009 | Anderson |
| 2009/0099404 A1 | 4/2009 | Kraus et al. |
| 2009/0138019 A1 | 5/2009 | Wasielewski |
| 2009/0165573 A1 | 7/2009 | Ledoux et al. |
| 2009/0177080 A1* | 7/2009 | Kristan ............. A61B 17/1707 600/424 |
| 2009/0227862 A1 | 9/2009 | Smith et al. |
| 2009/0306665 A1 | 12/2009 | Lerner et al. |
| 2009/0306666 A1 | 12/2009 | Czartoski et al. |
| 2009/0326537 A1 | 12/2009 | Anderson |
| 2010/0041985 A1 | 2/2010 | Simon et al. |
| 2010/0063508 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0100011 A1 | 4/2010 | Roche |
| 2010/0137869 A1 | 6/2010 | Borja et al. |
| 2010/0137871 A1 | 6/2010 | Borja |
| 2010/0145337 A1* | 6/2010 | Janna ................ A61B 17/1707 606/67 |
| 2010/0152566 A1* | 6/2010 | Rains ................ A61B 17/1707 600/409 |
| 2010/0152573 A1* | 6/2010 | Ritchey ................ A61B 5/05 600/424 |
| 2010/0210939 A1* | 8/2010 | Hartmann .......... A61B 19/5244 600/424 |
| 2010/0211177 A1 | 8/2010 | Abdou |
| 2010/0249657 A1 | 9/2010 | Nycz et al. |
| 2010/0261998 A1* | 10/2010 | Stiehl ..................... A61B 19/50 600/424 |
| 2010/0274121 A1* | 10/2010 | Ritchey ................ A61B 5/05 600/424 |
| 2010/0274253 A1 | 10/2010 | Ure |
| 2010/0274256 A1* | 10/2010 | Ritchey ................ A61B 5/05 606/96 |
| 2010/0274306 A1 | 10/2010 | Pastore et al. |
| 2010/0289491 A1 | 11/2010 | Budker et al. |
| 2010/0312245 A1* | 12/2010 | Tipirneni ............. A61B 17/742 606/62 |
| 2011/0082366 A1 | 4/2011 | Scully |
| 2011/0109311 A1 | 5/2011 | Walsh |
| 2011/0130765 A1 | 6/2011 | Fernandez |
| 2011/0208037 A1* | 8/2011 | Rains .................... A61B 5/064 600/409 |
| 2011/0257518 A1 | 10/2011 | Buly et al. |
| 2011/0270080 A1 | 11/2011 | Crane |
| 2011/0288600 A1 | 11/2011 | Ritchey |
| 2011/0295108 A1* | 12/2011 | Cox ....................... A61B 5/042 600/424 |
| 2011/0295253 A1 | 12/2011 | Bonutti et al. |
| 2012/0022406 A1 | 1/2012 | Hladio et al. |
| 2012/0029578 A1* | 2/2012 | Suh ................... A61B 17/7035 606/309 |
| 2012/0035468 A1 | 2/2012 | Ritchey et al. |
| 2012/0053585 A1* | 3/2012 | Nycz ................... A61B 8/0841 606/62 |
| 2012/0091122 A1* | 4/2012 | Ahmad ................. C21D 1/09 219/632 |
| 2012/0101361 A1 | 4/2012 | Rains |
| 2012/0136402 A1 | 5/2012 | Burroughs |
| 2012/0143047 A1 | 6/2012 | Kimura |
| 2012/0184844 A1 | 7/2012 | Gielen |
| 2012/0209117 A1 | 8/2012 | Mozes et al. |
| 2012/0220107 A1 | 8/2012 | Fukuda et al. |
| 2012/0226094 A1* | 9/2012 | Ritchey ............. A61B 17/1707 600/12 |
| 2012/0227542 A1 | 9/2012 | Koch |
| 2012/0232561 A1 | 9/2012 | Fernandez |
| 2012/0253354 A1* | 10/2012 | Arlettaz ............. A61B 17/1725 606/98 |
| 2012/0283599 A1 | 11/2012 | Borja |
| 2012/0330191 A1* | 12/2012 | Hulliger ................ A61B 90/06 600/587 |
| 2013/0018381 A1* | 1/2013 | Baumgartner ..... A61B 17/1707 606/96 |
| 2013/0079829 A1* | 3/2013 | Globerman ........ A61B 17/7233 606/286 |
| 2013/0131679 A1* | 5/2013 | Janna ................ A61B 17/1707 606/62 |
| 2013/0218007 A1* | 8/2013 | Petteys ............. A61B 17/1728 600/424 |
| 2013/0238036 A1* | 9/2013 | Sinha .................... A61B 17/68 606/304 |
| 2013/0289573 A1 | 10/2013 | Heilala |
| 2014/0081121 A1* | 3/2014 | Wilhelm ................ A61B 17/80 600/409 |
| 2015/0080893 A1* | 3/2015 | Graca ............... A61B 17/1707 606/64 |
| 2015/0245786 A1* | 9/2015 | Lee ........................ A61B 5/062 600/424 |
| 2015/0265368 A1* | 9/2015 | Chopra .................. A61B 5/062 600/424 |
| 2016/0029998 A1* | 2/2016 | Brister ................. A61B 5/6853 600/424 |

FOREIGN PATENT DOCUMENTS

| | | |
|---|---|---|
| CN | 201029876 Y | 3/2008 |
| DE | 102008023760 | 12/2009 |
| EP | 523905 | 5/1993 |
| EP | 628287 | 4/1995 |

(56) References Cited

FOREIGN PATENT DOCUMENTS

| | | |
|---|---|---|
| EP | 1382308 A2 | 1/2004 |
| EP | 1391181 | 2/2004 |
| EP | 1570782 | 9/2005 |
| EP | 1803394 | 7/2007 |
| EP | 1570781 | 9/2009 |
| EP | 2130511 | 12/2009 |
| EP | 1563810 | 3/2010 |
| EP | 1743590 | 10/2010 |
| GR | 1005791 | 1/2008 |
| JP | 2004130094 A | 4/2004 |
| WO | WO9500085 | 1/1995 |
| WO | WO9713467 | 4/1997 |
| WO | WO9832387 | 7/1998 |
| WO | WO9947052 | 9/1999 |
| WO | WO0134016 | 10/2001 |
| WO | WO02062250 | 8/2002 |
| WO | WO03044556 | 5/2003 |
| WO | WO03073951 | 9/2003 |
| WO | WO03041611 | 12/2003 |
| WO | WO03105659 | 12/2003 |
| WO | WO2004030556 | 4/2004 |
| WO | WO2004001569 | 7/2004 |
| WO | WO2004069063 | 8/2004 |
| WO | WO2004091419 | 11/2004 |
| WO | WO2004112610 | 12/2004 |
| WO | WO2005023110 | 3/2005 |
| WO | WO2005087125 | 9/2005 |
| WO | WO2005120203 | 12/2005 |
| WO | WO2006060632 | 6/2006 |
| WO | WO2006094119 | 9/2006 |
| WO | WO2005084572 A3 | 11/2006 |
| WO | WO2007009088 | 1/2007 |
| WO | WO2007025191 | 3/2007 |
| WO | WO2007061890 | 5/2007 |
| WO | WO2007133168 | 11/2007 |
| WO | WO2008105874 | 9/2008 |
| WO | WO2008106593 | 9/2008 |
| WO | WO2009046547 | 4/2009 |
| WO | WO2009108214 | 9/2009 |
| WO | WO2009131999 | 10/2009 |
| WO | WO2010011978 | 1/2010 |
| WO | WO2010028046 | 3/2010 |
| WO | WO2010099247 | 9/2010 |
| WO | WO2010111272 | 9/2010 |
| WO | WO2010124164 A1 | 10/2010 |
| WO | WO2010129141 | 11/2010 |
| WO | WO2010129308 | 11/2010 |
| WO | WO2011060536 | 5/2011 |
| WO | WO2011124661 | 10/2011 |
| WO | WO2012080840 | 6/2012 |
| WO | WO2013049534 | 4/2013 |

OTHER PUBLICATIONS

Office Action in Russian Application No. 2011146914, mailed Dec. 16, 2013.
Notice of Reasons for Rejection for Japanese Application No. 2012-508611, mailed Jan. 28, 2014.
European Search Report for European Application No. 07830964.7, mailed Jun. 18, 2010, 4 pages.
Office Action for Russian Application No. 2011146669/14 mailed Apr. 3, 2014, 5 pages.
Office Action for U.S. Appl. No. 13/358,065, mailed Jun. 3, 2014, 6 pages.
Extended European Search Report for European Application No. 12800328.2, mailed May 27, 2015.
Canadian Office Action for Application No. 2,678,369, mailed Sep. 4, 2015.
Notice of Reasons for Rejection in Japanese Application 2014-249827, mailed Oct. 5, 2015.
Office Action for Canadian Application No. 2,777,468, mailed Jan. 19, 2016.
Office Action for Canadian Application No. 2,759,694, mailed Feb. 17, 2016.
Second Office Action for Chinese Application No. 201080028779.8 mailed Apr. 10, 2015.
"Guiding Star with the LIDIS module," Ekliptik, 2007.
Ekliptik, LIDIS module, brochure, 2010.
Brochure for GE Healthcare Drapes and Sterile Covers, accessed on Jun. 21, 2012, at http://www.gehealthcare.com/usen/xr/surgery/docs/SurgeryDrapes&Film.pdf.
Ekliptik, "User Manual: Guiding Star/LIDIS," Jun. 16, 2010, reprinted from http://www.ekliptik.si/html/downloads/documents/manuals/LIDIS_user_manual.pdf.
Medtronic, "Orthopaedic Navigation Soluations," 2005, reprinted from http://behzadisportsdoc.com/wordpress/wp-content/uploads/2011/05/medtronic_orthonavsolutions.pdf.
GE Healthcare, "Interventional X-ray, OEC C-arm," 2012.
Ekliptik, Guiding Star, Lidis: The Best Solution for Distal Interlocking, 2008, 2 pages.
Ekliptik, "Guiding Star", reprinted from http://ekliptik.si/content/view/37/42, on Jul. 1, 2010, 2 pages.
International Preliminary Report on Patentability for International Application No. PCT/US2012/036320, mailed Nov. 12, 2013.
Office Action for U.S. Appl. No. 12/768,689, mailed Jul. 9, 2014.
First Office Action for Chinese Application No. 201080028779.8 mailed May 23, 2014.
Authorized officer Hee Gok Kang, International Search Report/Written Opinion in PCT/US2012/036320, mailed Nov. 20, 2012, 11 pages.
"ORIF—Axial compression plating" [online] [Retrieved on Apr. 23, 2012]; Retrieved from the Internet URL: https://www2.aofoundation.org/wps/portal/surgery?showPage=redfix&bone=Tibia&segment=Shaft&classification=42-A3&treatment=&method=ORIF%20-%20Open%20reduction%20internal%20fixation&implantstype=Compression%20plating&approach=&redfix_url=1285239037789&Language=en; 5 pages.
Office Action for U.S. Appl. No. 13/323,010, mailed Jan. 19, 2016.
Office Action in Canadian Application No. 2,759,694, mailed Feb. 17, 2016.

\* cited by examiner

TARGETING LANDMARKS OF ORTHOPAEDIC DEVICES

CROSS-REFERENCE TO RELATED APPLICATIONS

This application claims priority to and the full benefit of U.S. Provisional Application Ser. No. 61/483,228, filed May 6, 2011, and titled "Targeting Landmarks of Orthopaedic Devices," the entire contents of which are incorporated herein by reference.

TECHNICAL FIELD

This disclosure relates to targeting landmarks of orthopaedic devices.

BACKGROUND

Orthopaedic devices are used in the treatment of many injuries or conditions. For example, treatment of certain bone fractures involves stabilizing selected portions and/or fragments of bone using an implantable orthopaedic plate and/or an implantable orthopaedic nail, and various bone screws or pins. As another example, joints can be fused or otherwise immobilized using plates and/or nails secured with bone screws or pins.

In some instances, it is necessary or beneficial to target a hidden landmark of an orthopaedic implant. For example, some procedures involve placement of bone screws or pins through selected apertures of an implanted orthopaedic device. Such targeting can be accomplished in some cases using radiographic imaging. Unfortunately, radiographic imaging can be undesirable for various reasons. For example, exposure to radiation energy used in the imaging process can be harmful to a patient as well as to those treating the patient or assisting those treating the patient. Additionally, radiographic imaging can be expensive and time-consuming, as well as potentially inaccurate, or less accurate than desired.

Recent advances have seen an increase in the use of landmarks such as slotted holes and combination holes in bone plates and nails. These so-called combination holes, can include a partially-threaded portion and a non-threaded portion that is used for compression of the bone in a particular direction. Drill guides or other mechanical targeting devices have been used for targeting different hole positions within these combination holes, but these methods can be time consuming and difficult for surgeons to manipulate the mechanical targeting devices during surgery.

Recently, electromagnetic-based targeting of orthopaedic implants has been employed to determine relative locations and orientations of tools and features, such as landmarks, of an implanted orthopaedic device. For example, distal locking holes of an implanted intramedullary nail can be targeted for drilling and fixation using a locking screw with an electromagnetic targeting system, such as the TRIGEN® SURESHOT® distal targeting system offered by SMITH & NEPHEW®. However, these targeting systems have not been used for targeting multiple hole locations within, for example, a combination or slotted hole, to allow surgeons to achieve optimal positioning of bone screws or pins for controlled compression of a bone fracture.

SUMMARY

In one general aspect, a targeting system can be used to target a particular location of a landmark of an orthopaedic implant. The landmark can be hole, and the targeting system can be used to target one of multiple different locations in the hole.

In another general aspect, an apparatus includes one or more processing devices and one or more storage devices storing instructions that are operable, when executed by the one or more processing devices, to cause the one or more processing devices to perform operations. The operations include receiving signals from a magnetic sensor located at a known position relative to an orthopaedic implant, the orthopaedic implant defining a hole that admits a transfixion element, the hole being defined to admit a transfixion element at two or more targeting locations in the hole. The operations include selecting a first targeting location of the two or more targeting locations. The operations include determining, based on the signals, a position of a landmark identifier relative to the first targeting location. The operations include indicating the position of the landmark identifier relative to the first targeting location.

Implementations may include one or more of the following features. For example, the two or more targeting locations include a targeting location in a threaded region of the hole and a targeting location in a non-threaded region of the hole. Determining, based on the signals, the position of the landmark identifier relative to the selected first targeting location includes: accessing information about characteristics of the orthopaedic implant; and accessing information about the position of the magnetic sensor relative to the orthopaedic implant. Determining the position of the landmark identifier relative to the first targeting location is further based on the information about the characteristics of the orthopaedic implant and the position of the magnetic sensor relative to the orthopaedic implant. The operations include: receiving second signals from the magnetic sensor; determining, based on the second signals, a position of the landmark identifier relative to a second targeting location of the two or more targeting locations; and indicating the position of the landmark identifier relative to the second targeting location. Indicating the position of the landmark identifier relative to the first targeting location includes indicating a location for installing a non-locking fastener, and indicating the position of the landmark identifier relative to the second targeting location includes indicating a location for installing a locking fastener.

Implementations may also include one or more of the following features. For example, the operations include: receiving second signals from the magnetic sensor; determining, based on the second signals, a position of the landmark identifier relative to a second targeting location in a second hole; and indicating the position of the landmark identifier relative to the second targeting location. The first targeting location is offset from a central location of the hole. The hole is defined to include an elongated region and a circular region. The circular region has a diameter, the elongated region includes a length and a width, and the length is greater than the diameter. The two or more targeting locations include at least one of a center point of the elongated region and a center point of the circular region. Selecting the first targeting location includes receiving user input and selecting the first targeting location based on the user input. Selecting the first targeting location includes: accessing information indicating an amount of bone compression; and selecting, as the first targeting location, a location at which insertion of a transfixion element will cause the amount of bone compression.

In another general aspect, a method for facilitating a bone compression procedure includes determining a position of an instrument relative to a target location using an electromagnetic targeting system, the target location being located in a hole defined in an orthopaedic implant, the hole being defined to admit a transfixion element at two or more locations in the hole. The method includes displaying, on a display device, representations of the orthopaedic implant, the hole, and the target location. The method includes indicating, on the display device, the position of the instrument relative to the target location. The method includes indicating, on the display device, an amount of compression to a bone fracture corresponding to the target location.

Implementations may include one or more of the following features. For example, the method further includes receiving user input, and in response, to receiving the user input, changing the target location from a first location of the two or more locations to a second location of the two or more locations. Receiving user input includes receiving user input that indicates a specified amount of bone compression. Changing the target location from a first location of the two or more locations to a second location of the two or more locations includes: determining, as the second location, a location at which insertion of a transfixion element will cause the specified amount of bone compression; and indicating, on the display device, the position of the instrument relative to the second location.

In another general aspect, a system includes an electromagnetic field generator and an orthopaedic implant defining at least one hole that defines two or more targeting locations for receiving a transfixion element, the orthopaedic implant having a magnetic sensor located at a known location relative to at least one of the two or more locations. The system includes a landmark identifier and a control unit. The control unit is configured to: select, as a target location, one of the two or more locations; receive signals from the magnetic sensor; determine a position of the landmark identifier relative to the target location based on the received signals; and indicate the position of the landmark identifier relative to the target location.

In another general aspect, a method for targeting a landmark of an orthopaedic implant includes implanting the orthopaedic implant in a body, the orthopaedic implant having at least one landmark defining two or more locations for targeting and a first magnetic sensor located at a known distance from at least one of the two or more locations, identifying one of the locations using a landmark identifier, the landmark identifier having at least one of a second magnetic sensor and a magnetic field generator, installing a transfixion element in the at least one landmark, and identifying a second location using the landmark identifier.

Implementations may include one or more of the following features. For example, the method further includes installing a second transfixion element in the at least one landmark. The landmark is a hole including an elongated portion and a circular portion. The elongated portion includes a length and a width, and the circular portion has a diameter, and the length is greater than the diameter. The two or more locations may include at least one of a center point of the elongated portion and a center point of the circular portion. The transfixion element includes a non-locking screw and the second transfixion element includes a locking screw. The implant is at least one of a nail and a plate.

In another general aspect, a method for targeting a hole defined in an orthopaedic implant includes implanting the orthopaedic implant in a body, the orthopaedic implant including a bone plate defining at least one hole defining two or more locations for targeting and a first magnetic sensor located at a known distance from at least one of the two or more locations, identifying one of the locations using a landmark identifier, the landmark identifier having at least one of a second magnetic sensor and a magnetic field generator, installing a non-locking fastener in the one of the locations, identifying a second location of the at least one hole using the landmark identifier, and installing a locking fastener in the second location of the at least one hole.

Implementations may include one or more of the following features. For example, the hole includes an elongated portion and a circular portion. The two or more locations include at least one of a center point of the elongated portion and a center point of the circular portion.

In another general aspect, a method for targeting a hole with multiple hole locations includes implanting an orthopaedic implant in a patient, the orthopaedic implant including at least one of an orthopaedic plate and an intramedullary nail defining at least one hole defining two or more hole positions for targeting, an elongated portion and an at least partially-threaded circular portion, and a first magnetic sensor disposed at a known distance from at least one of the hole positions, identifying at least one of the hole positions in the elongated portion using a landmark identifier, the landmark identifier including at least one of a second magnetic sensor and magnetic field generator, installing a non-locking screw in the at least one of the hole positions in the elongated portion, identifying at least one of the hole positions in the circular portion using the landmark identifier, and installing a locking screw in the at least one of the hole positions in the circular portion.

Implementations may include one or more of the following features. For example, the method further includes two or more bones or bone fragments coupled to the implant, and installing the non-locking screw includes compressing the bones or bone fragments. The method further includes removing the non-locking screw after installing the locking screw. The first magnetic sensor is located in at least one of a pocket in the plate or nail, a recess in the plate or nail, a probe and an instrument coupled to the plate or nail.

In another general aspect, a method for targeting a hole defining multiple hole positions includes providing an orthopaedic implant assembly having an orthopaedic plate defining at least one first hole defining two or more hole positions for targeting and an elongated portion and a threaded circular portion, a second hole and a third hole, and a first magnetic sensor located at a known distance from at least one of the hole positions, the second and third holes, implanting the orthopaedic implant assembly in a patient so that each of the second hole and the third hole is positioned on opposite sides of a bone fracture, installing a first transfixion element in one of the second and the third holes to engage a bone, identifying at least one of the hole positions in the elongated portion using a landmark identifier having at least one of a second magnetic sensor and magnetic field generator, installing a non-locking screw in the at least one of the hole positions in the elongated portion, and installing a second transfixion element in one of the threaded circular portion and the other of the second and the third holes.

Implementations may include one or more of the following features. For example, the method further includes identifying at least one of the hole positions in the threaded circular portion. The first transfixion element and the second transfixion element include locking screws.

In another general aspect, a method for compressing a bone fracture includes implanting an orthopaedic implant in a patient, the orthopaedic implant including at least one feature and an associated first magnetic sensor, identifying a particular position in the feature using a landmark identifier, the landmark identifier including at least one of a second magnetic sensor and a magnetic field generator, and installing a transfixion element in the particular position in the feature.

Implementations may include one or more of the following features. For example, identifying the particular position in the feature includes inputting a compression value in a computer. The method further includes moving the orthopaedic implant axially or transversely during installation of the transfixion element in the particular position. The method further includes moving the orthopaedic implant axially or transversely after installing the transfixion element in the particular position. Inputting the compression value includes at least one of relocating a visual indicator on a user interface and touching an indicator arrow. At least one or more compression values are associated with at least one of the visual indicator and the indicator arrow and change in response to one of the relocation of the visual indicator and touching of the indicator arrow. The visual indicator is located inside the feature. The implant includes a nail or a plate. The method further includes installing a second transfixion element prior to the installation of the first transfixion element. The first and second transfixion elements are installed in opposite bone fragments. The first sensor is located in at least one of a probe and a nail.

In another general aspect, a method for compressing a bone fracture includes implanting an orthopaedic implant in a patient, the orthopaedic implant including at least a first non-oblong hole, a second non-oblong hole, and an associated first magnetic sensor, identifying a position distanced from a center point of the first non-oblong hole using a landmark identifier including at least one of a second magnetic sensor and magnetic field generator, installing a first transfixion element in the position to compress the bone fracture, identifying a second position distanced from a center point of the second non-oblong hole using the landmark identifier, and installing a second transfixion element in the second position to further compress the bone fracture.

Implementations may include one or more of the following features. For example, the first and second non-oblong holes include one of a threaded hole, non-threaded hole, or a combination thereof. The transfixion elements are non-locking screws. The compression is axial or transverse. The orthopaedic implant is a bone plate. The first and second non-oblong holes include one of circular and square holes.

In another general aspect, a method for facilitating a bone compression procedure using an electromagnetic targeting system includes displaying, on a display device, an image of an orthopaedic implant, at least one landmark associated with the implant, and at least one target associated with the landmark, and displaying, on the display device, at least one of on-screen controls for adjusting an amount of compression to a bone fracture and values indicative of an amount of compression to a bone fracture.

Implementations may include one or more of the following features. For example, values indicative of an amount of compression to a bone fracture are displayed, and the values include at least one of input values and output values. The input values are at least one of a measurement, a distance, and an amount of bone compression. The values include output values that indicate a relative position of the target to at least a portion of the landmark. The method further includes receiving input values and changing a position of the target based on the input values. The method further includes moving a landmark identifier represented by a visual indicator on the screen into alignment with the target associated with the landmark on the screen. The landmark is at least one of a hole and a slot. The target is a position for a screw. One or more on-screen controls are displayed, and the method further includes receiving data indicative of a user interaction with the one or more on-screen controls and changing a position of the target based on the user interaction with the on-screen controls.

In another general aspect, a method for displaying a graphical user interface includes displaying a graphical depiction of an orthopaedic implant including at least one of a hole including an elongated portion and a threaded portion and a slot, and displaying at least one graphical feature permitting a user to move a target location for a non-locking screw along a longitudinal axis of at least one of the elongated portion and the slot.

Implementations may include one or more of the following features. For example, the method further includes displaying at least one of icons indicative of an amount of compression to a bone fracture and values indicative of an amount of compression to a bone fracture. The method further includes displaying one or more controls, receiving data indicating user interaction with the one or more controls, and in response to the user interaction with the one or more controls, changing the target position for the non-locking screw relative to the elongated portion or the slot, thereby changing the amount of compression to be applied to the bone fracture.

The details of one or more implementations are set forth in the accompanying drawings and the description below. Other features, objects, and advantages of the disclosure will be apparent from the description and drawings, and from the claims.

DETAILED DESCRIPTION

Figure 1:
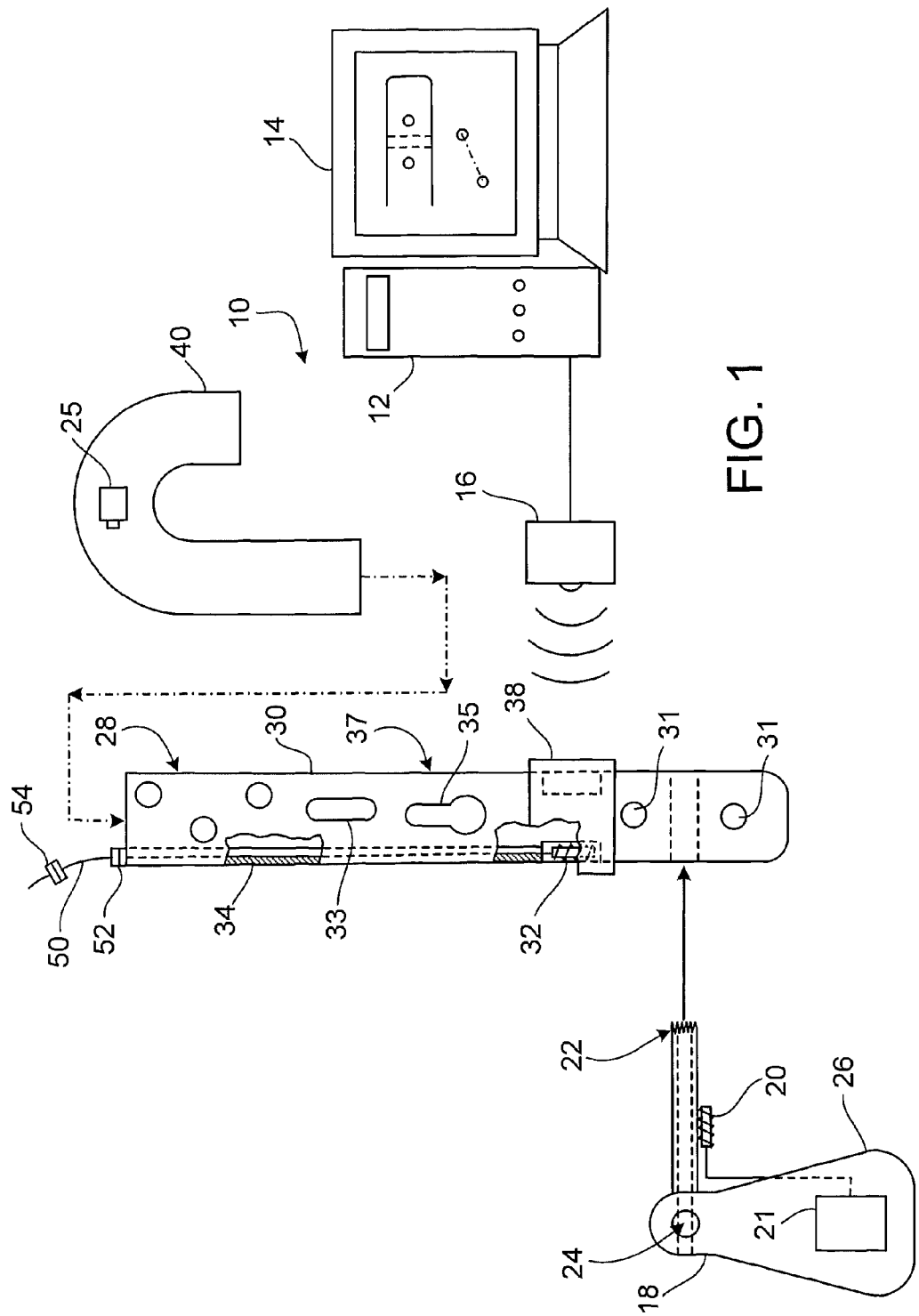
FIG. 1 illustrates a system for identifying a landmark of an orthopaedic implant.

Referring to the accompanying drawings in which like reference numbers indicate like elements, FIG. 1 illustrates one disclosed system 10 for identifying a landmark. The system 10 may include a control unit 12, a magnetic field generator 16, a landmark identifier 18, and an orthopaedic implant assembly 28. The system 10 may also include a monitor 14 electrically connected to the control unit 12 and an insertion handle 40 removably attached to the orthopaedic implant assembly 28.

The control unit 12 may include hardware, software, or a combination of hardware and software. The control unit 12 is depicted as a desktop computer in FIG. 1 but other types of computing devices may be used. As examples, the control unit 12 may be a desktop computer, a laptop computer, a personal data assistant (PDA), a mobile handheld device, a dedicated device, or other processing device. The control unit 12 controls the magnetic field generator 16 and receives signals from magnetic sensors, for example, small mobile inductive sensors, either by wire or wirelessly. The control unit 12 may also communicate with one or more other processing devices.

The magnetic field generator 16 may be a device available from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other generators may be used. As examples, the magnetic field generator 16 may provide a pulsed direct current electromagnetic field or an alternating current electromagnetic field.

The system 10 is a magnetic spatial tracking system. For illustrative purposes, the magnetic field generator 16 may include suitably arranged electromagnetic coils that define reference positions in a spatial reference frame (e.g., defining orthogonal axes X, Y, Z of a coordinate system). The system 10 may also include one or more magnetic sensors, which are attached to the objects being tracked. The magnetic sensors can include one or more of, for example, an inductive coil, a Hall effect sensor, a fluxgate magnetic field sensor, and a magneto-resistive sensor. Other variants, such as other types of sensors, could be easily accommodated. The position (e.g., location and/or angular orientation) of the magnetic sensors are determined from the magnetic coupling between the magnetic sensors and the source field produced by magnetic field generator 16.

The magnetic field generator 16 generates spatial magnetic field shapes, or distributions, which are sensed by the magnetic sensors. The magnetic sensors produce signals responsive to the magnetic fields. The control unit 12 processes the signals to determine the position (e.g., location and/or orientation) of the respective magnetic sensors, and hence the positions of the objects to which the respective magnetic sensors are mounted. Positions are determined relative to the spatial reference frame, which, as noted above, is defined relative to the magnetic field generator 16. The control unit 12 may use the coordinate reference system and the sensed data to create a transformation matrix including position information (e.g., location information and/or orientation information).

The landmark identifier 18 is used to target a landmark, such as a landmark on the orthopaedic implant assembly 28. In some implementations, the landmark identifier 18 emits and/or detects magnetic fields in a manner that its position can be determined in the spatial reference frame. The landmark identifier 18 may include one or more magnetic sensors or may include the field generator. The landmark identifier 18 may comprise any number of devices. The landmark identifier 18 can be a device that includes a structure that provides a user with an understanding of the location and orientation of a hidden landmark. For example, the landmark identifier 18 can include a drill guide, a drill sleeve, a drill, a drill nose, a drill barrel, a drill chuck, or a fixation element. In some implementations, the structure that indicates the location and orientation of a landmark can be a housing having an opening, or another other structure.

In FIG. 1, the landmark identifier 18 is a drill sleeve and includes a sensor 20. The landmark identifier 18 may include one or more of a serrated tip 22, a tube 24, and a handle 26. The tube 24 also may be referred to as a bushing, a cylinder, a guide, or a drilling/screw placement guide. The tube 24 may receive a drill bit or other tool. The sensor 20 has a fixed position relative to an axis, such as a central longitudinal axis, of the tube 24. The fixed position of the sensor 20 from the tube 24 and a known offset between the sensor and the axis allow the spatial position of the tube to be determined in six degrees of freedom (e.g., three translational and three angular) relative to the magnetic field generator 16 and/or another sensor in the system. The control unit 12 can be calibrated to adjust for the offset distance and orientation of the sensor 20 and, for example, an end of the tube 24. The landmark identifier 18 and the magnetic field generator 16 may be combined into a single component. For example, the magnetic field generator 16 may be incorporated within the handle 26.

The orthopaedic implant assembly 28 may include an implant 30 and one or more magnetic sensors. The orthopaedic implant assembly 28 includes a first sensor 32. In FIG. 1, the implant 30 is in the form of intramedullary nail but other types of implants may be used. As examples, the implant may be an intramedullary nail, a bone plate, a shoulder prosthetic, a hip prosthetic, or a knee prosthetic. The first sensor 32 is oriented and in a predetermined position relative to one or more landmarks on the implant 30. As examples, the landmark may be a structure, a void, a boss, a channel, a detent or indentation, a flange, a groove, a member, a partition, a step, an aperture, a bore, a cavity, a dimple, a duct, a gap, a notch, an orifice, a passage, a slit, a hole, or a slot. In FIG. 1, the landmarks may include transfixion holes 31, slotted holes, such as slotted hole 33, and combination holes, such as combination hole 35. The fixed position of the first sensor 32 from the landmarks and the known offset between the sensor 32 and the landmarks allow the position of the landmarks to be determined in six degrees of freedom (three translational and three angular) relative to the magnetic field generator 16 or another sensor in the system, such as the sensor 20. The control unit 12 can be calibrated to adjust for the offset distance and orientation of the first sensor 32 relative to the orthopaedic implant assembly 28.

Figure 1A:
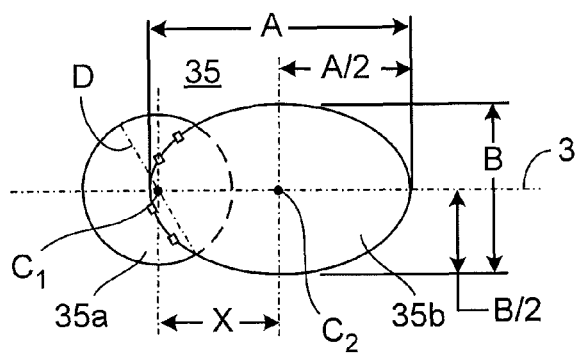
FIG. 1A is a schematic representation of a combination hole of the orthopaedic implant of FIG. 1.

As shown schematically in FIG. 1A, the combination hole 35 of FIG. 1 may include a first, substantially circular portion 35a, and a second, elongated portion 35b. The circular portion 35a and the elongated portion 35b overlap one another, and are thus in communication with one another. In another implementation, the combination hole may include two, substantially circular portions, each overlapping one another, and in communication with one another. The perimeter or outer periphery of circular portion 35a defines a first center point $C_1$, and a diameter D. The perimeter or outer periphery of elongated portion 35b defines a second center point $C_2$. The outer periphery of elongated portion 35b also defines a length or major axis A and a width or minor axis B substantially perpendicular to the major axis A. Major axis A may be substantially parallel to a longitudinal axis 3 of, for example, a bone plate. In addition, major axis A may lie on longitudinal axis 3 with first and second center points $C_1$, $C_2$ located on longitudinal axis 3, however other configurations are possible. Major axis A is greater than D.

Still referring to FIG. 1A, first center point $C_1$ and second center point $C_2$ are separated from one another by a distance X, which is less than the sum of D/2 and A/2. In some implementations, distance X satisfies the following exemplary condition:

$$0.5(D/2+A/2)<X<1.0(D/2+A/2)$$

According to another implementation, diameter D is less than minor axis B. Diameter D may satisfy the following conditions:

$$0.75B \leq D \leq 1.1B$$

As will be discussed in further detail below, elongated portion 35b may be configured and dimensioned to receive a substantially spherical screw-head. Elongated portion 35b may have a concave, substantially spherical recess that opens toward upper surface of the implant 30. When the shaft of a bone screw having a spherical head is located eccentrically in elongated portion 35b, the spherical head may engage the recess and bias the bone plate to provide compression of the bone fracture in a desired direction.

Referring to FIG. 1, the first sensor 32 and the second sensor 20 are coupled to the control unit 12. This may be accomplished by wire or wirelessly. The first sensor 32 and the second sensor 20 may be a six degree of freedom sensor configured to describe the position of each sensor with respect to three translational axes, generally called X, Y and Z and three angular orientations, generally called pitch, yaw and roll. By locating the sensor in this manner, and knowing the location and orientation of each sensor, the landmark identifier 18 may be located relative to the landmark on the implant 30. In one particular implementation, the information from the sensors allows for a surgeon to plan the surgical path for fixation and properly align a drill with a blind fixation hole 31. Each sensor 32, 20 can be, for example, a six degree of freedom sensor from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other sensors may be used.

The first sensor 32 may be attached to the implant 30. For example, the first sensor 32 may be attached to an outer surface 37 of the implant 30. The implant 30 may also include a groove 34 and a pocket 36 (see FIG. 2). The groove 34 and pocket 36 are located in a wall of the implant 30. The first sensor 32 is intended to be attached to the implant 30 and may be installed in a patient for the service life of the implant 30. Further, the orthopaedic implant assembly 28 may include a cover 38 to cover the pocket 36 and/or the groove 34. The cover 38 may be substantially flush with the external surface 37 of the implant 30. Accordingly, the implant 30 may include a second opening 39 (see FIG. 2) to receive the cover 38.

The first sensor 32 may be tethered to leads for communication and power. The leads, and the sensor, may be fixed to the implant 30. A lead 50 may be used to connect the first sensor 32 to the control unit 12. The lead 50 may be made from biocompatible wire. As an example, the lead 50 may be made of DFT wire available from Fort Wayne Metals Research Products Corp., 9609 Indianapolis Road, Fort Wayne, Ind. 46809. DFT is a registered trademark of Fort Wayne Metals Research Products Corp. A first connector 52 may be used to place the lead 50 relative to the implant 30. A second connector 54 may be used to connect the lead 50 to another device, such as the control unit 12 or the insertion handle 40.

The first sensor 32 may be fixed in the pocket 36 using a range of high stiffness adhesives or polymers including epoxy resins, polyurethanes, polymethyl methacrylate, polyetheretherketone, UV curable adhesives, silicone, and medical grade cyanoacrylates. As an example, EPO-TEK 301 available from Epoxy Technology, 14 Fortune Drive, Billerica, Mass. 01821 may be used. The lead 50 may be fixed in the groove in a similar manner. These types of fixation methods do not adversely affect the performance of the electrical components. Thereafter, the cover 38 may be placed on the implant 30 and welded in-place. For example, the covers may be laser welded to the implant. The lead 50 may also be placed in a groove (not shown) that includes one or more portions formed at intermittent locations along the length of the groove to receive the lead 50 to rigidly and mechanically capture the lead 50 and the associated first sensor 32 in a fixed position relative to the implant 30.

The monitor 14 may be configured to display the position (e.g., location and/or orientation) of the first sensor 32 and the second sensor 20 so that the display may show a surgeon both sensor positions relative to one another. The control unit 12 may send positional data, either by wire or wirelessly, to a user interface, which may graphically display the relative positions of the landmark identifier 18 and the implant 30 on the monitor. The view displayed on the monitor 14 may be oriented relative to the landmark identifier 18 so that the surgeon may visualize the user interface as an extension of the landmark identifier 18. The user interface also may be oriented so that the surgeon may view the monitor and the surgical field simultaneously.

The insertion handle 40 may be used for installation of the orthopaedic implant assembly 28 and also may be used to route the leads from the first sensor 32. For example, the insertion handle 40 may route both communication and power leads between the implant 30 and the control unit 12.

In FIG. 1, the landmark identifier 18 and the insertion handle 40 each include a communications module 21, 25 for wirelessly transmitting data from the sensor 20, 32 to the control unit 12, but other methods, such as wired communications, may be used. The second connector 54 plugs into the communications module 25. Alternatively, and as is explained in greater detail below, the implant 30 and the insertion handle 40 may have mating electrical contacts that form a connection when the components are assembled such that the first sensor 32 is connected to the communications module 25.

The implant 30 may include a communications circuit and an antenna for wireless communication. Power for the first sensor 32 and/or the communications circuit may be positioned within the insertion handle 40. For example, a battery may be placed within the insertion handle 40 for transferring power to the first sensor 32 and/or other electronics. Alternatively, the communications circuit, the antenna, and the battery may be located within the insertion handle 40 and each of these may be tethered to the first sensor 32. In yet another implementation, the implant 30 may include a coil to inductively power the communications circuit and communicate data from the first sensor 32. The power source may be a single source mode or may be a dual mode AC/DC.

In general use, the orthopaedic implant assembly 28 is installed in a patient. For example, in the case of internal fixation, the intramedullary nail is placed within an intramedullary canal. Optionally, the user may use transfixion elements, such as screws, to first lock the proximal end of the intramedullary nail. An operator uses the landmark identifier 18 and the first sensor 32 to identify the landmarks. For example, in the case of intramedullary nail fixation, a surgeon uses the landmark identifier 18 to identify the blind transfixion holes 31 and drill through the holes 31 for placement of a transfixion element.

Figure 2:
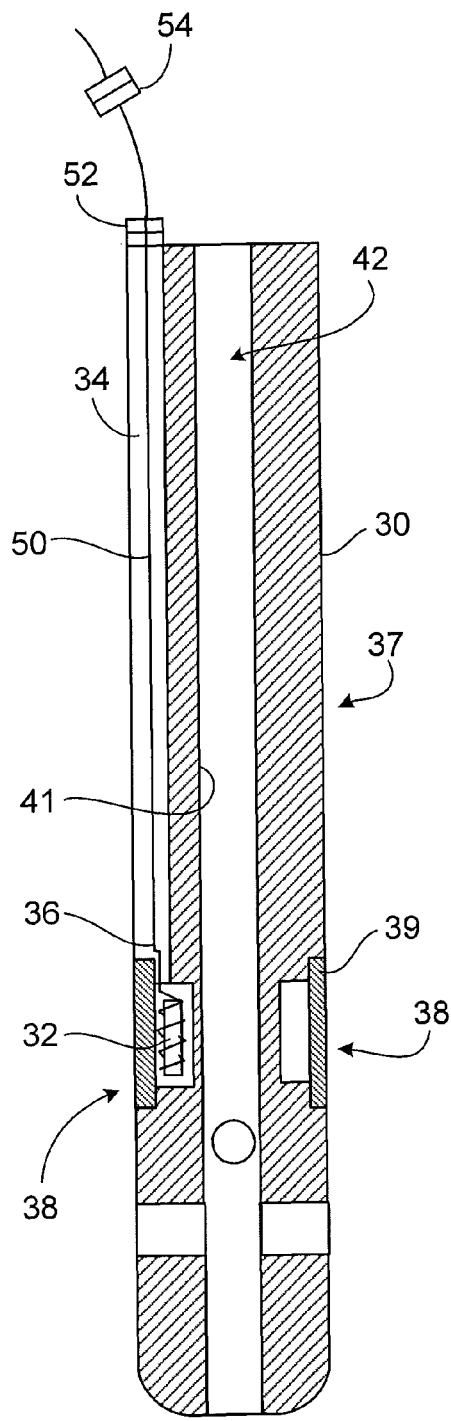
FIG. 2 is a sectional view of an orthopaedic implant of FIG. 1 illustrating a sensor assembly.

FIG. 2 further illustrates the implant 30 as illustrated in FIG. 1. The implant 30 includes the first sensor 32, the longitudinal groove 34, the pocket 36, the cover 38, and the second opening 39. The implant 30 also has an outer surface 37. The cover 38 may be comprised, for example, of gold or titanium foil. The implant 30 may include an inner surface 41 that defines a cannulation 42.

Figure 3:
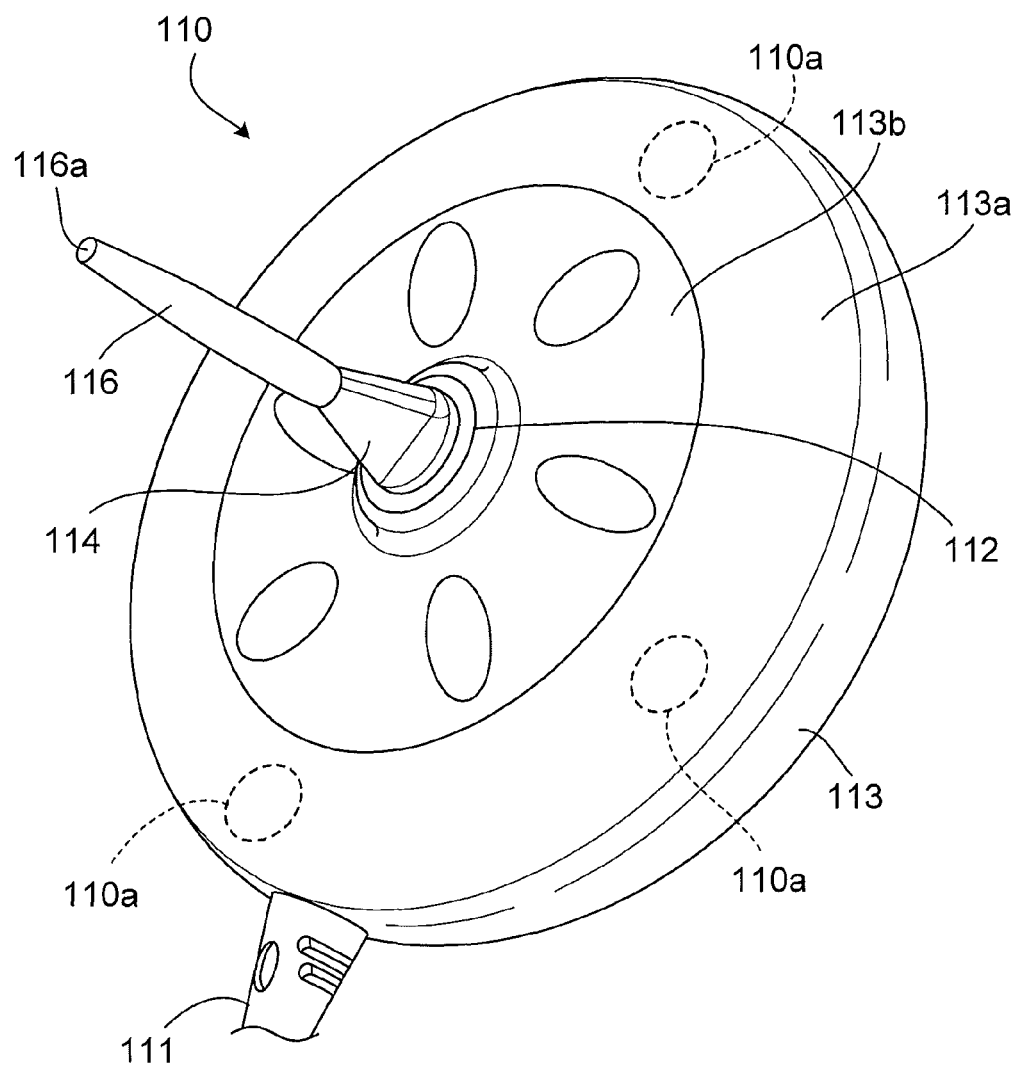
FIG. 3 illustrates an alternative implementation of a landmark identifier.

FIG. 3 illustrates an alternative implementation of a landmark identifier that combines functionality of the landmark identifier 18 and the magnetic field generator 16 of FIG. 1 with a removable component, such as a drill sleeve or drill guide 116, into a handheld landmark identifier 110 that may be used in the system 10. The handheld landmark identifier 110 includes an electromagnetic field generator 110a within a housing 113 that includes one or more induction coils or other elements to create a suitable electromagnetic field or fields. The generated electromagnetic fields can be detected by one or more electromagnetic sensors, such as sensor 32, and, based on the output of the sensors, the position (including the location and the orientation) of the sensors relative to the landmark identifier 110 can be determined.

The electromagnetic field generator 110a is mounted in or on an autoclavable material and encapsulated in an autoclavable housing body 113 that may be easily sterilized. The housing body 113 includes a coupling member 112 that passes through the internal body and the housing 113 and removably engages one or more attachable components, such as drill guide 116 having a serrated tip 116a, or other suitable tools, such as a screw driver sleeve or other drill sleeves as selected by a surgeon. The housing body 113 includes a first covering 113a formed from an autoclavable material, such as an overmolding of silicone material, and may include a second covering 113b that provides an additional layer of protection or insulation, or aesthetics at an outer edge of the housing 113. The second covering 113b may be formed from an autoclavable material similar or different than the first covering 113a.

The landmark identifier 110 can include a wired or wireless link to a processor or control unit, such as control unit 12, or to a control unit included as part of monitor 14 (FIG. 1) to receive power and control signals to control the operation of the electromagnetic field generator 110a. For example, the landmark identifier 110 can include a cable 111 that provides a connection to the control unit or monitor 14.

Unlike the landmark identifier 18 illustrated in FIG. 1, the handheld landmark identifier 110 does not require the sensor 20 because the origin of the global coordinate reference system (the area in which the electromagnetic field is generated) can be defined within the landmark identifier 110. For example, one axis of the global coordinate reference system can be the longitudinal axis of the drill sleeve 116 or other component. In that situation, the other two axes of the global coordinate reference system can be defined by planes orthogonal to that longitudinal axis and to each other. An advantage of incorporating the field generator into the landmark identifier 110 includes a smaller size field generator because it can be brought into the local working space (e.g, the area which may include the landmarks such as implant holes that are to be targeted for screw placement), therefore requiring a smaller electromagnetic field. In addition, use of the landmark identifier 110 may reduce or eliminate the need for X-ray devices for targeting of transfixion elements, such as radiation-emitting, fluoroscopic "c-arms," which have been used to achieve proper distal screw placement during insertion of tibial and femoral nails.

The useful range of the landmark identifier 110 is a three-dimensional region around the landmark identifier 110, referred to as the working volume of the landmark identifier 110. The size and shape of the working volume is based on the characteristics of the electromagnetic fields produced by the electromagnetic field generator 110a and can be modified to be larger or smaller based on the need for targeting accuracy. For example, when targeting a hole in an intramedullary nail, it may be desirable to have high degree of accuracy due to the fact that the hole is hidden inside a bone. In addition, when targeting a combination hole or slotted hole to achieve a desired amount of compression, it may be desirable to have a high degree of accuracy. In some implementations, the working volume is smaller as a result of increasing the degree of accuracy. For targeting a hole in some bone plates, it may not be necessary to have very high degree of accuracy due to the location of the hole of the bone plate outside a bone, where it can be exposed for visual confirmation of its location. As a result, the working volume can be made much larger than in some intramedullary nail targeting applications. The larger working volume makes it possible to target a larger number of holes in the working volume. In some implementations, the working volume is a volume that surrounds the landmark identifier 110. For example, the landmark identifier 110 can be generally centrally located within the working volume, and the working volume for some implementations, such as targeting holes of a bone plate, can extend approximately 50 cm or more in width and approximately 40 cm or more in depth and located at a distance of about 5 cm from the landmark identifier 110. A drill sleeve, for example, will typically have a length of more than 5 cm to ensure that it is positioned within the working volume. As will be appreciated by one of skill in the art, however, multiple working volume values are achievable based on surgical procedures and equipment set up.

Figure 4:
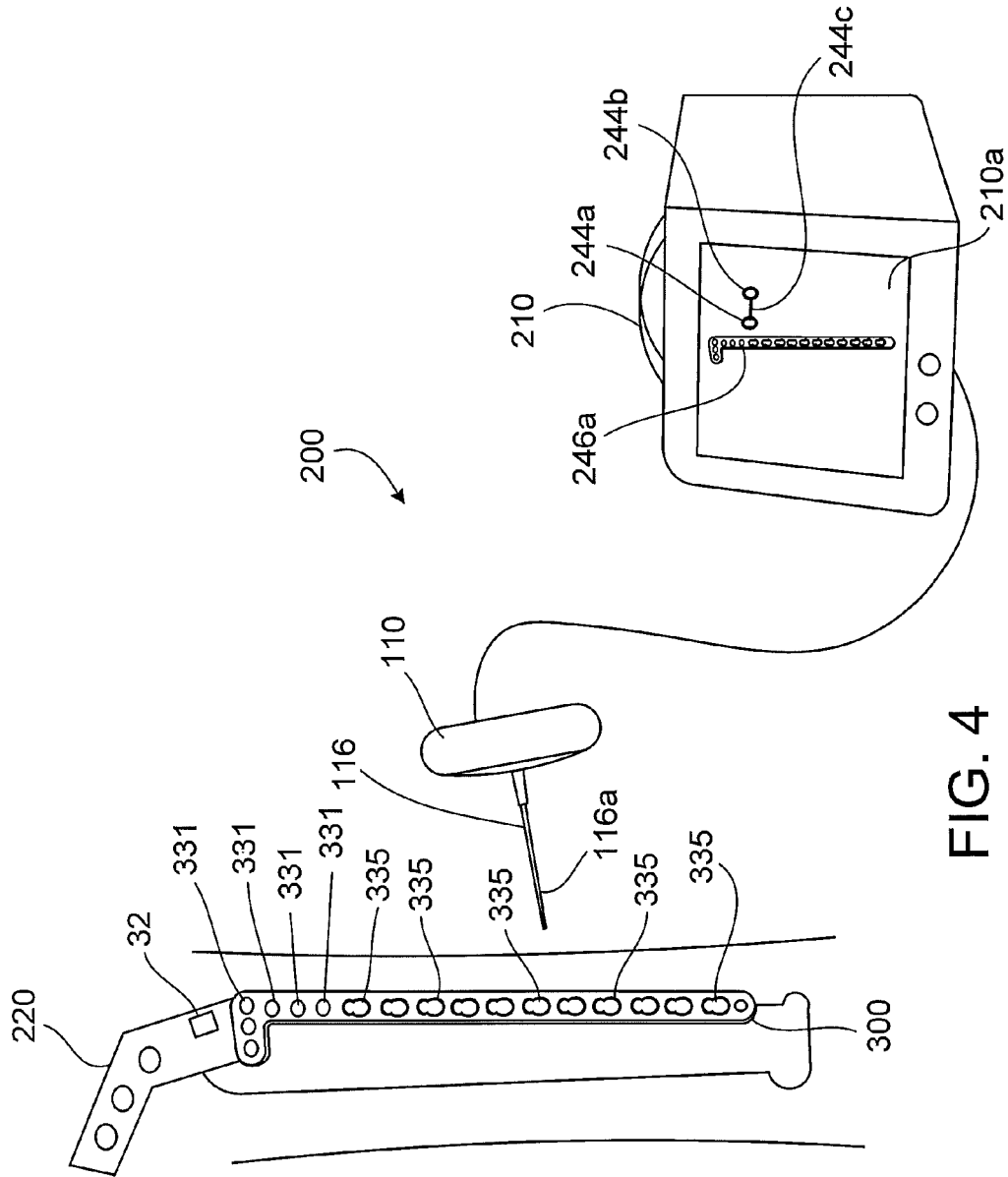
FIG. 4 is a perspective view of a system for targeting landmarks.

Referring to FIG. 4, a targeting system 200 includes a control unit 210, the landmark identifier 110, and an insertion handle 220 coupled to an orthopaedic implant, such as bone plate 300. The bone plate 300 can be attached to a fractured bone to provide alignment, compression, and support for bone portions during a healing process. As other examples, orthopaedic devices that can be targeted using the system 200 include intramedullary nails, bone plates, prosthetic joint components, and external fixation devices. In addition, although landmark identifier 110 is shown, targeting system 200 could also be used with a landmark identifier, such as landmark identifier 18 of FIG. 1.

The bone plate 300 includes multiple landmarks, such as transfixion holes 331 and combination holes 335. Other landmarks can include structures, voids, bosses, channels, detents, flanges, grooves, members, partitions, steps, apertures, bores, cavities, dimples, ducts, gaps, notches, orifices, passages, slits, holes, slots, and elongated holes or slots. The landmarks may also include variable-angle holes, variable-angle locking holes, or fixed-angle locking holes, or combinations of these types of holes.

The insertion handle 220 may be used to maneuver the bone plate 300 during implantation in a patient. The insertion handle 220 is removably coupled to the bone plate 300, so that the insertion handle 220 can guide the bone plate 300 during implantation and then be removed from the bone plate 300 after implantation has been completed. Other methods of maneuvering the bone plate 300 during implantation may be used, such as, for example, drill guides, posts, or other suitable means, and are within the knowledge of those skilled in the art.

The insertion handle 220 couples to the bone plate 300 at a fixed position relative to the bone plate 300. The insertion handle 220 includes an electromagnetic field sensor 32, similar to the sensor 32 of FIG. 1, that responds to electromagnetic fields produced by the landmark identifier 110. The sensor 32 is attached to the insertion handle 220 at a known, fixed position of the insertion handle 220. Thus, when the insertion handle 220 is attached to the bone plate 300, the position of the sensor 32 relative to the bone plate 300 is known in six degrees of freedom, and the sensor 32 is disposed at a known location and orientation relative to the landmarks, such as transfixion holes 331 and combination holes 335. Other means of attaching or coupling the sensor 32 to the bone plate 300 so that the position of the sensor 32 is known in all six degrees of freedom are known may be employed, such as attaching the sensor 32 to a known position on the bone plate 300 or coupling the sensor 32 to the bone plate 300 using any of the methods previously described herein.

If the position of the sensor 32 on the insertion handle 220 is not initially known in one or more degrees of freedom, the sensor 32 can be calibrated using a second sensor (not shown) attached to the bone plate 300 with a known location and orientation relative to a landmark of the bone plate 300 or relative to a known landmark of the insertion handle 220. Alternatively, the landmark identifier 110 can be attached to the bone plate 300 at a known location and orientation relative to a landmark of the bone plate 300 or relative to a known landmark of the insertion handle 220. In some implementations, the sensor 32 of the insertion handle 220 can be shipped in a pre-calibrated state such that upon attachment of the insertion handle 220 to the bone plate 300, the position of the sensor 32 relative to the landmarks of the bone plate 300 is known for six degrees of freedom.

During the implantation process and afterward, the precise location and orientation of tools, such as drill bits, pins, screws, or other devices may need to be known relative to the landmarks, and specifically relative to positions within the landmarks, such as within combination holes 335 of the bone plate 300. Unlike typical round holes formed in orthopaedic implants, combination holes 335 include an elongated portion (35b of FIG. 1A) coupled to a circular portion (35a of FIG. 1A) which is threaded 180 degrees or more and the distance between the center point of the elongated portion and the center point of the circular portion can be less than the sum of the radius (of the circular portion) and the major radius (of the elongated portion). These landmarks, however, may be covered by tissue and may be difficult to locate. Additionally, jigs or other means for determining the location of a tool and/or the angle of the tool relative to the implant or landmark may be difficult and time consuming to determine, and may not provide the desired degree of accuracy.

Moreover, often in the case of bone plates, the surgeon would like to know how much compression the surgeon may achieve based on the particular location of, for example, a compression-type screw within the elongated portion of the combination hole 335 prior to placement of a locking screw or a screw with a deformable head in a circular hole to lock the plate to the bone. The landmark identifier 110 in conjunction with software running on a processor of the control unit 210 can be used to target a predetermined point within, for example, the elongated portion of the combination hole 335 or an elongated slot in the bone plate 300 based on the known parameters of the bone plate 300, the location of the landmarks on the bone plate 300, location and type of fracture, and the known location and degrees of freedom of the associated sensor 32.

Depending on the point chosen for locating the tool within the combination hole 335, the control unit 210 may also provide an indication (e.g., numerically, graphically, or otherwise) via a user interface 210a of control unit 210 of the amount of compression attained for the particular bone fracture in conjunction with the chosen bone plate 300 to allow the surgeon to either increase or decrease the amount of compression in order to optimize the healing and recovery process. Thus, the landmark identifier 110 in conjunction with the control unit 210 may be used to target landmarks, and in particular, specific locations within landmarks, such as specific points within an elongated portion of combination holes 335, to determine the position of transfixion elements placed in the landmarks and attainable characteristics, such as bone compression, when the landmarks are exposed or when the landmarks are covered by tissue.

The control unit 210 of the system 200 controls the operation of the landmark identifier 110 and receives inputs from the sensor 32. The control unit 210 also includes a user interface 210a that provides information to an operator of the system 200. The control unit 210 includes a processor that is configured to determine the location and orientation of the sensor 32 relative to landmarks of the orthopaedic implant, such as bone plate 300 based on the input from the sensor 32 and information regarding the signal that controls the electromagnetic field generator 110a. The determination is made based on a known positional relationship between the sensor 32 and the landmarks and a determined position of the landmark identifier 110 relative to the sensor 32.

The control unit 210 can access pre-programmed information about the shape of the orthopaedic implant, such as bone plate 300, and the locations of the features of the bone plate 300. In particular implementations, the control unit 210 can access other information about the orthopaedic implant, such as a three-dimensional models of the bone plate 300, dimensions of the bone plate 300, calculations of center points of the elongated portion and circular portions of combination holes 335 of the bone plate 300, and positions and dimensions of other transfixion holes or slots formed in the bone plate 300. Additionally, the control unit 210 can access information regarding the location(s) of sensor(s) 32. For example, as discussed above, the sensor(s) 32 can be attached to pre-selected landmarks, handles, or other items attached at positions or configurations relative to the implant, or information regarding the landmarks to which the sensor(s) 32 are attached can be input to the control unit 210, such as by a user touching a portion of the interface 210a to indicate a landmark to which the sensor(s) 32 are attached.

As described further below, the control unit 210 receives signals from the sensor 32, which is located at a known position relative to the orthopaedic implant 300. Each combination hole 335 of the orthopaedic implant 300 is defined to admit a transfixion element at two or more targeting locations in the combination hole 335. The control unit 210 selects a first targeting location of the two or more targeting locations. The selected first targeting location may be, for example, a center point of a circular portion or a center point of an elongated portion of the combination hole 335. The first targeting location 210 can be selected based on user input that identifies the location, based on calculations of a location that will result in a desired amount of bone compression, and/or other input. The control unit 210 determines, based on the signals from the sensor 32, a position of the landmark identifier 110 relative to the first targeting location, and indicates the position of the landmark identifier 110 relative to the first targeting location, for example, on a user interface.

Referring to FIGS. 4 and 5A-5C, the landmark identifier 110 and the control unit 210 can be used to target multiple locations within, for example, combination holes 335 of the bone plate 300. To target a first position or location, for example, a center 350 (FIG. 5A) of an elongated portion 335b of the combination hole 335 or a center 360 (FIG. 5A) of a circular portion 335a, the landmark identifier 110 is positioned near the bone plate 300, such as with a tip 116a of the drill guide 116 in contact with the patient's skin. When the sensor 32 is located within the working volume of the landmark identifier 110, and the electromagnetic field generator 110a produces an electromagnetic field, the control unit 210 receives signals produced by the sensor 32 that indicate the position of the sensor 32 relative to the landmark identifier 110. Using the signals from the sensor 32, the control unit 210 can determine the position of the landmark identifier 110 relative to the targeted combination hole 335 of the bone plate 300. The control unit 210 outputs information about the position of the landmark identifier 110 relative to the targeted combination hole 335, and in some instances, relative to the centers 350, 360 or other desired feature locations of the combination hole 335 of the bone plate 300 on the user interface 210a.

Based on the user interface 210a, a surgeon or other user can place the landmark identifier 110 in a position where the interface 210a indicates that the tip 116a of the drill guide 116 is directly above a selected position within the combination hole 335 of the bone plate 300. For example, in some implementations, the interface 210a includes a first identifier element 244a, such as a first circle, that indicates a position of the distal tip 116a of the drill guide 116. Thus, when the first identifier element 244a is in alignment with a landmark element 246a that corresponds to, and represents a targeted position, such as a center point 350 of the elongated portion 335b or a center point 360 of the circular portion 335a, the interface 210a indicates that the tip 116a of the drill guide 116 is directly above either center point 350, 360 represented by the combination hole 335. The interface 210a can also include different graphical elements, and can include audio or haptic outputs.

When the location of the desired position or location within the combination hole 335 is known, the combination hole 335 can be exposed, such as by making an incision in the area of the tip 116a of the drill guide 116 when the first identifier element 244a is aligned with the landmark element 246a as indicated on the user interface 210a. A provisional fixation pin, a non-locking bone screw, a locking bone screw, or a variable locking bone screw can then be engaged with the patient's bone and/or the combination hole 335. Additionally, a drill or other tool can be used to create a hole in the patient's bone to receive one or more of the fasteners mentioned above. The landmark identifier 110 and the control unit 210 may then be used to engage another one of a provisional fixation pin, non-locking screw, locking bone screw, or a variable locking bone screw in another desired location within the same combination hole 335 or another landmark in the bone plate 300.

Figure 5A:
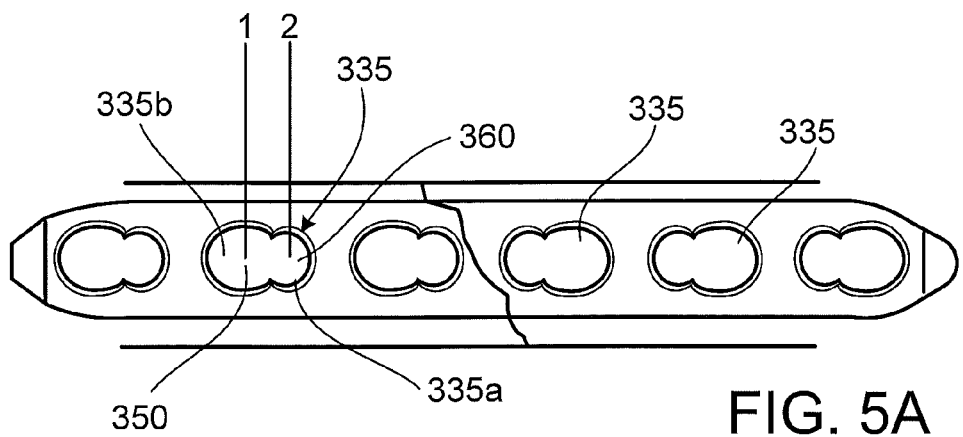
FIGS. 5A-5C illustrate various sequences by which transfixion elements may be placed within combination holes using a landmark identifier.
Figure 5B:
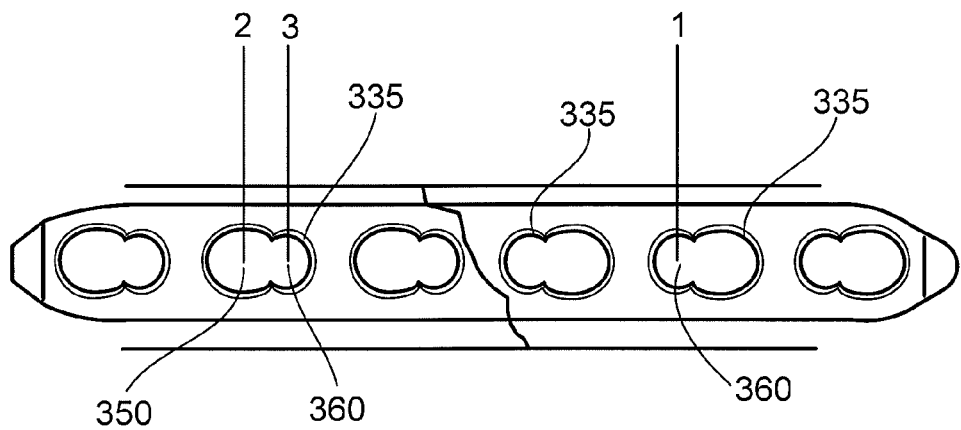
Figure 5C:
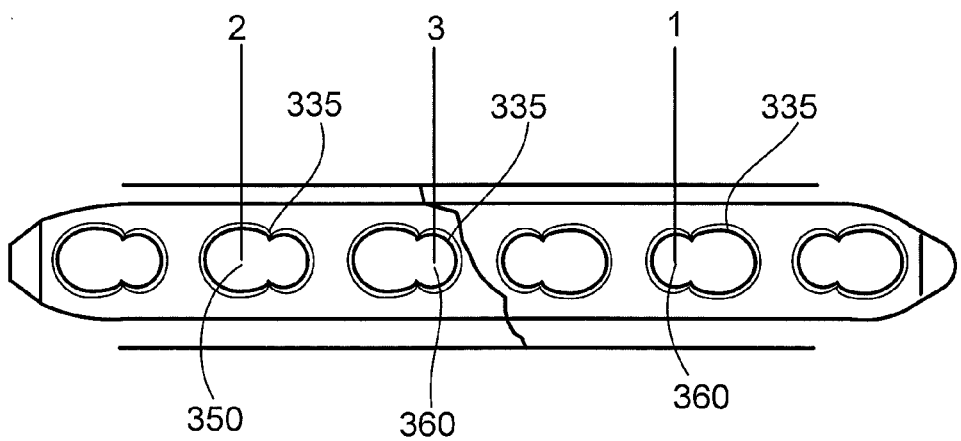

FIGS. 5A to 5C illustrate schematically various exemplary views of user interface 210a illustrating sequences by which fixation members, such as provisional fixation pins, non-locking screws, locking bone screws, or variable locking bone screws may be placed within combination holes 335 using the landmark identifier 110 or 18 and the control unit 210 as described above. For example, as illustrated schematically in FIG. 5A, after coupling the plate to a bone fragment on one side of the fracture via any means know to one skilled in the art, a user can use the landmark identifier 110 and the control unit 210 to first place a non-locking screw at position "1" located off the center point 350 of the elongated portion 335b of combination hole 335 to move the plate toward the left and compress the fracture, and then place a locking bone screw at position "2" located at the center point 360 of the circular portion 335a of the combination hole 335.

Likewise, FIG. 5B illustrates a second implementation where a user may use the landmark identifier 110 and the control unit 210 to first place a locking bone screw at position "1" located at the center point 360 of the circular portion 335a of a first combination hole 335. The user may then place a non-locking compression screw at position "2" located off the center point 350 of the elongated portion 335b of a second combination hole 335 to compress the fracture and finally may then place a locking screw at position "3" located at the center point 360 of the circular portion 335a of the second combination hole 335.

FIG. 5C shows yet another exemplary implementation where a user may use the landmark identifier 110 and the control unit 210 to first place a locking bone screw at position "1" located at the center point 360 of the circular portion 335a of a first combination hole 335 and then place a non-locking compression screw at position "2" located off the center point 350 of the elongated portion 335b of a second combination hole to compress the fracture. Then the user may use the landmark identifier 110 and the control unit 210 to place a locking bone screw at position "3" located at the center point 360 of the circular portion 335a of a third combination hole 335. Each of the implementations shown in FIGS. 5A-5C may result in slightly varied compression and bone healing characteristics, and therefore, the implementations described herein provide the user with a number of different options in order to optimize healing and recovery.

Figure 6:
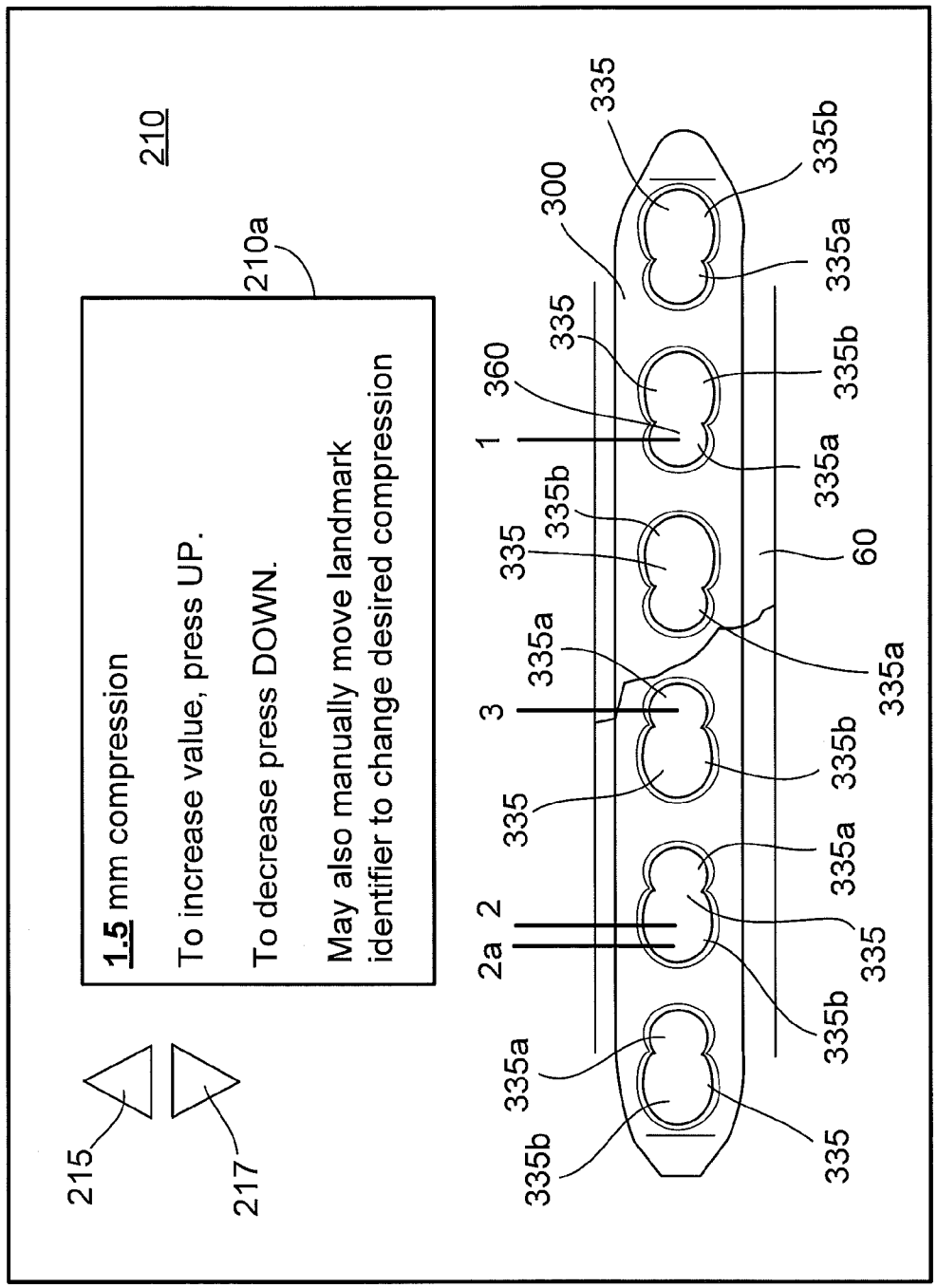
FIG. 6 illustrates an exemplary user interface of a control unit for use with a landmark identifier.

FIG. 6 illustrates an exemplary implementation of the user interface 210a and illustrates how one of the landmark identifiers 18, 110 may be used in conjunction with the control unit 210 to insert a fixation element, such as a screw, provisional pin, or the like, in a particular position within a slot or combination hole in order to provide controlled compression of a bone fracture. The particular position may be a position determined to be optimal by the operator or the control unit 210. Referring to FIG. 6, a portion of the bone plate 300 is shown on the user interface 210a placed across a graphical depiction of a bone fracture 60. The bone plate 300 includes a number of combination holes 335, each having a circular portion 335a and an elongated portion 335b. As described above, a user may use the landmark identifier 110 and the control unit 210 to place transfixion elements, such as screws or provisional pins at various locations within the combination holes 335 using the techniques described above.

As shown in the exemplary implementation of FIG. 6, a user first places a locking screw at position "1" using the landmark identifier 110 and the control unit 210 to locate the locking screw in the center point 360 of the circular portion 335a of a first combination hole 335. Once the locking screw is in position "1," the user may then proceed to place a compression-type screw into the elongated portion 335b of a second combination hole 335 as shown generally at position "2" off its center for compression. As shown in the exemplary implementation of FIG. 6, if the user placed the compression screw at position "2" then the screw allows for 1.5 mm of compression to the bone fracture 60 based on calculations by the software. If, however, the user desires to provide more or less compression to the bone fracture 60, then the user has at least two options. Accordingly, one can use the combination of screw(s) and plate to achieve bone compression.

The first option is that the user may depress an UP arrow 215 to increase the amount of compression or a DOWN arrow 217 to decrease the amount of compression. As an example, as shown in FIG. 6, if the user depresses the UP arrow, then the targeting line for position "2" changes position on the user interface 210*a* from position "2" to position "2a" and indicates to the user that the new position for the location of the fastening member within the elongated portion 335*b* of the combination hole 335 has moved to the left of the center of the elongated portion 335*b*. In addition to moving the target from position "2" to position "2a," the control unit 210 recalculates the amount of compression for the new position of the fixation member and will present that new value to the user (e.g., 2.0 mm, 2.5 mm, etc.) It should be apparent to one of skill in the art, that both the locations and values for compression will vary based on the dimensions and shapes of the orthopaedic implant (nail, plate, screw, etc.), the type of bone and/or bone fracture, location of fracture or compression, and the location of the fastening member within the hole and/or along the length of the orthopaedic implant. Providing the values of compression attainable at various positions within the elongated portions of the combination holes or other elongated slots formed in the orthopaedic implants helps to limit or prevent over-compression or under-compression of a bone fracture which aids in the avoidance of shortening of a bone or non-unions. In addition, such placement guidance aids in avoiding placement of fasteners at positions that are too close or too far from the edges of the slots or elongated portions which can result in minimal to no compression of the bone fracture.

As a second option, the user may simply move the landmark identifier from, for example, position "2" depicted by the identifier on the user interface 210*a* to position "2a" depicted by the identifier on the user interface 210*a*. It should be understood by one of skill in the art, that although the identifier is illustrated as a line on FIG. 6, the identifier can be one or more of the targeting identifier elements described above, or could include a cross-hair or other type of target element known in the art. As the user moves the landmark identifier 110 relative to the bone plate 300, and more particularly, relative to the position within the elongated portion 335*b* of the combination hole 335, the control unit 210 recalculates the resultant amount of compression that will be applied to the bone fracture 60 and presents that to the user via the user interface 210*a*. In this manner, both options provide the user with the ability to optimize the amount of compression by selectively locating the transfixion element within the elongated portions of the combination holes 335 of the bone plate 300. Finally, as described above, once the user has selected the desired position for the compression screw, then the user may use the landmark identifier 110 and the control unit 210 to place an additional locking screw at position "3" within the circular portion 335*a* of the combination hole 335 as depicted on FIG. 6.

The user interface 210*a* can also assist an operator to perform procedures in addition to inserting a transfixion element. For example, the user interface 210*a* can indicate positions for implanting a reinforcing element such as a plate hole-filling device into a vacant hole. As another example, the user interface 210*a* can guide the operator in locating transfixion elements to be removed. The user interface 210*a* can indicate the location of a removal tool relative to installed transfixion elements, and whether the position of the removal tool is acceptable for removing a particular transfixion element. The user interface 210*a* can indicate when the orientation of the removal tool is acceptable, for example, when the removal tool is aligned along an axis of the transfixion element.

In addition, the user interface 210*a* can indicate which combination holes 335 or other holes have been filled with transfixion elements. In some implementations, the operator can provide user input indicating which holes and/or which portion(s) of a combination hole 335 are occupied. In response, the control unit 210 indicates the holes or locations as being occupied. In some implementations, the control unit 210 may detect the locations at which transfixion elements are inserted as the transfixion elements are installed. After detecting installation of a transfixion element at a particular location, the control unit 210 may automatically indicate on the user interface 210*a* that the particular location (e.g., a particular hole or portion of a hole) is occupied.

Referring to FIG. 4, the landmark identifiers 18, 110 and the control unit 210 may also be used to compress fractures of bones via a step-wise or eccentric drilling method by identifying positions at a distance from a center point of circular or circular-like transfixion holes 331 of an orthopaedic implant such as bone plate 300 and provide incremental compression in each transfixion hole to obtain a target compression sum. Transfixion holes 331 may include threaded holes, non-threaded holes or combinations thereof, such as combination threaded and non-threaded holes as described in U.S. Pat. No. 7,905,910, which is incorporated herein by reference in its entirety, and may be circular, square, polygonal, or any combinations thereof. In use, with such orthopaedic implants, the landmark identifier, such as landmark identifier 110 and control unit 210 are used to identify a position at a distance from a center point of a first of the transfixion holes 331 and if the value of compression attainable at that position is less than the desired amount, then the user may identify a second position at a distance from a second one of the transfixion holes 331 and if the sum of the values of the compression attainable at that position and the previous position, as indicated on the user interface 210*a*, is the desired amount then the user or surgeon can choose to place a locking screw to lock the plate to the bone.

In addition to the features described above, the interface 210*a* of the control unit 210 can also indicate a current angular position of the landmark identifier 110 relative to the bone plate 300 or, for example, a combination hole 335 within the bone plate 300, to confirm acceptable positioning of a tool relative to the bone plate 300. For example, the control unit 210 can display a current angle of the drill guide 116 relative to a variable angle locking hole of the bone plate 300 so that an operator, such as a surgeon, can confirm that a hole drilled in the patient's bone will result in an acceptable angle for a variable angle locking fastener. In some implementations, the interface 210*a* includes a second identifier element 244*b*, such as a second circle, that represents a proximal portion of the landmark identifier 110, and a third identifier element 244*c* that represents an axis from the first identifier element 244*a* to the second identifier element 244*b*. As illustrated in FIG. 4, as the first identifier element 244*a* and the second identifier element 244*b* approach one another, the angle of the landmark identifier 110 approaches zero degrees from a reference axis, such as a central through-axis of a hole of the bone plate 300. Thus, when the first identifier element 244*a* and the second identifier element 244*b* are concentric, the landmark identifier 110 is parallel to the reference axis.

The control unit 210 receives a signal that indicates a position of the landmark identifier 110 relative to a landmark of the orthopaedic implant 30 or 300. The signal can be received from the sensor 32. Using the signal from the sensor 32, the control unit 210 determines the position of the tool relative to the landmark. The control unit 210 also compares the position of the tool to an acceptable range of positions, such as a range of acceptable positions of a fastener relative to the landmark. For example, landmark can be a variable angle locking hole, and the fastener can be a bone screw configured for variable-angle locking in the variable-angle hole. The variable-angle locking screw and variable-angle locking hole may have a limited range of angles for which use is approved, or indicated for a given procedure. As another example, when the tool includes a drill bit, the control unit 210 can compare an angle of the drill bit relative to a central through axis of the variable-angle locking hole to an acceptable insertion angle of the variable-angle locking hole. Additionally, a particular medical procedure may require that a fastener be inserted at a particular angle or position relative to the landmark. For example, a surgeon or other individual may determine that a particular bone fragment is disposed at a first angle relative to a variable angle locking hole or a non-locking hole. The control unit 210 can be used to identify when the landmark identifier 110 is targeting the bone fragment such that the bone fragment can be captured and secured by a fastener.

In some implementations, the control unit 210 outputs on the graphical user interface 210a an indication that the position of the landmark identifier 110 relative to a landmark is acceptable. For example, the output on the user interface 210a can include one or more elements, such as an element representing the angle of the landmark identifier 110 relative to an axis of the landmark, one or more elements representing acceptable positions of the landmark identifier 110 relative to the landmark, one or more elements representing unacceptable positions of the landmark identifier 110 relative to the landmark, a numeric representation of the angle of the landmark identifier 110 relative to an axis of the landmark, a numeric representation of the maximum acceptable insertion angle of a fastener, an element indicating that the current position of the landmark identifier 110 is acceptable, a graphical representation of an acceptable conical range of a variable angle or variable angle locking screw, and an element indicating that the current position of the landmark identifier 110 is unacceptable.

In some implementations, the control unit 210 determines whether a surgical orientation presents a risk to a patient. For example, the control unit 210 may determine whether a current position of the landmark identifier 110 relative to the orthopaedic implant 30 or 300 creates an unacceptable risk of injury to the patient. For example, when installing a distal screw in a distal radius plate, the control 210 can warn the operator when a position of the landmark identifier 110 is determined to present an unacceptable risk of breaching the articular surface. These techniques can be used to guide the operator to anatomically acceptable positions for drilling or insertion of transfixion elements when placing distal radius plates, proximal tibia plates, distal tibia plates, and other orthopaedic implants 30 or 300.

The control unit 210 can access data that indicates ranges of acceptable positioning for a procedure. The control unit 210 can access data about acceptable positioning for various different procedures and for different orthopaedic implants 30 or 300. The control unit 210 compares the position of the landmark identifier 210 relative to the orthopaedic implant 30 or 300 to the corresponding range of acceptable positioning for the particular procedure and particular orthopaedic implant 30 or 300. If the control unit 210 determines that the position of the landmark identifier 110 is outside the predetermined region of acceptability, the operator of the system can be warned so that injury or undesired outcomes are avoided. If the control unit 210 determines that the position of the landmark identifier 110 is acceptable, the control unit 210 can provide confirmation that the position is acceptable.

In some implementations, such as when a particularly large orthopaedic implant 30 is used, some landmarks of the orthopaedic implant 30 may be too far from the first sensor 32 to be targeted using the first sensor 32. In such implementations, among others, a second sensor (not shown) can be attached to the orthopaedic implant 30 at a location within the working volume shared by the first sensor 32 for use in targeting the landmarks that are too far from the first sensor 32 or outside the working volume. The second sensor can be attached to the orthopaedic implant 30 through a small incision, which may have been made using the landmark identifier and the first sensor 32 to reduce the number and size of incisions required to accomplish fixation of the orthopaedic implant 30.

In other implementations, a targeting system includes a large flat field generator disposed under the body part or the fractured bone. The targeting system also includes two sensors, one coupled to the implant and the other coupled to a drill sleeve, for example. If the generated field is larger than the volume of the largest implant intended to be used with the system, no additional sensors will be needed to target all of the landmarks of the plate.

A number of implementations and alternatives have been described. Nevertheless, it will be understood that various modifications may be made without departing from the spirit and scope of the disclosure. For example, although various of the methods of use have been described above with respect to the landmark identifier 110 of FIG. 3, it should be understood that these methods can also be carried out using the landmark identifier 18 of FIG. 1. In addition, although numerous features of the system have been described, the systems and methods described herein may also be used in accordance with the landmark identifiers, sensors, and control units described in WIPO International Publication Nos. WO2008/106593 and WO2009/108214, and as described in U.S. patent application Ser. Nos. 12/758,747 and 12/768,689, each of which is incorporated herein by reference in its entirety. Accordingly, other implementations are within the scope of the following claims.

What is claimed is:
1. An apparatus comprising:
one or more processing devices and one or more storage devices storing instructions that are operable, when executed by the one or more processing devices, to cause the one or more processing devices to perform operations comprising:
receiving signals from a magnetic sensor located at a known position relative to an orthopaedic implant, the orthopaedic implant defining a hole that admits a transfixion element, the hole being defined to admit a transfixion element at two or more targeting locations in the hole;
selecting a first targeting location of the two or more targeting locations, wherein selecting the first targeting location comprises:
accessing information indicating an amount of bone compression; and
selecting, as the first targeting location, a location at which insertion of a transfixion element will cause the amount of bone compression;

determining, based on the signals, a position of a landmark identifier relative to the first targeting location; and indicating the position of the landmark identifier relative to the first targeting location.

2. The apparatus of claim 1, wherein the hole is defined to include an elongated region and a circular region.

3. The apparatus of claim 2, wherein the circular region has a diameter, the elongated region comprises a length and a width, and the length is greater than the diameter.

4. The apparatus of claim 3, wherein the two or more targeting locations comprise at least one of a center point of the elongated region and a center point of the circular region.

5. The apparatus of claim 1, wherein the operations further comprise:

receiving second signals from the magnetic sensor;

determining, based on the second signals, a position of the landmark identifier relative to a second targeting location of the two or more targeting locations; and indicating the position of the landmark identifier relative to the second targeting location.

6. The apparatus of claim 5, wherein:

indicating the position of the landmark identifier relative to the first targeting location comprises indicating a location for installing a non-locking fastener; and indicating the position of the landmark identifier relative to the second targeting location comprises indicating a location for installing a locking fastener.

7. The apparatus of claim 1, wherein the two or more targeting locations comprise a targeting location in a threaded region of the hole and a targeting location in a non-threaded region of the hole.

8. The apparatus of claim 1, wherein determining, based on the signals, the position of the landmark identifier relative to the first targeting location comprises:

accessing information about characteristics of the orthopaedic implant; and accessing information about the position of the magnetic sensor relative to the orthopaedic implant; and wherein determining the position of the landmark identifier relative to the first targeting location is further based on the information about the characteristics of the orthopaedic implant and the position of the magnetic sensor relative to the orthopaedic implant.

9. The apparatus of claim 1, wherein the operations further comprise:

receiving second signals from the magnetic sensor;

determining, based on the second signals, a position of the landmark identifier relative to a second targeting location in a second hole; and indicating the position of the landmark identifier relative to the second targeting location.

10. The apparatus of claim 1, wherein the first targeting location is offset from a central location of the hole.

11. The apparatus of claim 1, wherein selecting the first targeting location comprises:

receiving user input; and selecting the first targeting location based on the user input.

12. A method for targeting a landmark of an orthopaedic implant, the method comprising:

implanting the orthopaedic implant in a body, the orthopaedic implant having at least one hole defining two or more locations for targeting and a first magnetic sensor located at a known distance from at least one of the two or more locations;

identifying a first location of the two or more locations using a landmark identifier, the landmark identifier having at least one of a second magnetic sensor and a magnetic field generator;

installing a transfixion element in the at least one hole at the identified first location; and after the transfixion element has been installed and while the transfixion element is in the at least one hole, identifying a second location of the two or more locations using the landmark identifier.

13. The method of claim 12, wherein the hole comprises an elongated portion and a circular portion.

14. The method of claim 13, wherein the elongated portion comprises a length and a width, and the circular portion has a diameter, and the length is greater than the diameter.

15. The method of claim 13, wherein the two or more locations comprise at least one of a center point of the elongated portion and a center point of the circular portion.

16. The method of claim 12, further comprising installing a second transfixion element in the at least one hole at the identified second location.

17. The method of claim 16, wherein the second transfixion element comprises a locking screw.

18. The method of claim 12, wherein the transfixion element comprises a non-locking screw.

19. The method of claim 12, wherein the implant is at least one of a nail and a plate.

20. The method of claim 12, wherein identifying the first location of the two or more locations using a landmark identifier comprises:

identifying, as the first location, a target location of the two or more locations that corresponds to a predetermined amount of compression of bone fragments of a fractured bone of the body.

21. A method for facilitating a bone compression procedure, the method comprising:

determining a position of an instrument relative to a target location using an electromagnetic targeting system, the target location being located in a hole defined in an orthopaedic implant, the hole being defined to admit a transfixion element at two or more locations in the hole;

displaying, on a display device, representations of the orthopaedic implant, the hole, and the target location;

indicating, on the display device, the position of the instrument relative to the target location; and indicating, on the display device, an amount of compression to be applied between bone fragments of a fractured bone by insertion of a transfixion element at the target location.

22. The method of claim 21, further comprising:

receiving user input; and in response to receiving the user input, changing the target location from a first location of the two or more locations to a second location of the two or more locations.

23. The method of claim 22, wherein:

receiving user input comprises receiving user input that indicates a specified amount of bone compression; and changing the target location from a first location of the two or more locations to a second location of the two or more locations comprises:

determining, as the second location, a location at which insertion of a transfixion element will cause the specified amount of bone compression; and indicating, on the display device, the position of the instrument relative to the second location.

24. A system comprising:

an electromagnetic field generator;

an orthopaedic implant defining at least one hole that defines two or more targeting locations for receiving a transfixion element, the orthopaedic implant having a magnetic sensor located at a known location relative to at least one of the two or more locations;

a landmark identifier; and a control unit configured to:
- access information indicating an amount of bone compression;
- select, from among the two or more locations, a target location at which insertion of a transfixion element will cause the amount of bone compression;
- receive signals from the magnetic sensor;
- determine a position of the landmark identifier relative to the target location based on the received signals; and
- indicate the position of the landmark identifier relative to the target location.

* * * * *